US007635754B2

(12) United States Patent
Boisvert et al.

(10) Patent No.: US 7,635,754 B2
(45) Date of Patent: Dec. 22, 2009

(54) INTERLEUKIN-9 AND INTERLEUKIN-4 CHIMERIC ANTAGONIST MUTEINS AND METHODS OF USING SAME

(75) Inventors: David C. Boisvert, El Cerrito, CA (US); Malinda Longphre, Oakland, CA (US); Teresa M. Wong, Lafayette, CA (US); Sydney M. Zaremba, Alameda, CA (US)

(73) Assignee: Aerovance, Inc., Berkeley, CA (US)

( * ) Notice: Subject to any disclaimer, the term of this patent is extended or adjusted under 35 U.S.C. 154(b) by 135 days.

(21) Appl. No.: 11/026,396

(22) Filed: Dec. 29, 2004

(65) Prior Publication Data

US 2006/0063236 A1    Mar. 23, 2006

Related U.S. Application Data

(60) Provisional application No. 60/612,275, filed on Sep. 22, 2004.

(51) Int. Cl.
*C07K 14/52* (2006.01)
*C12N 15/00* (2006.01)

(52) U.S. Cl. .............. 530/351; 435/69.1; 435/69.5; 435/69.7

(58) Field of Classification Search ............... None
See application file for complete search history.

(56) References Cited

U.S. PATENT DOCUMENTS

| 5,011,912 A | 4/1991 | Hopp et al. |
| 5,225,212 A | 7/1993 | Martin et al. |
| 5,314,695 A | 5/1994 | Brown |
| 5,395,619 A | 3/1995 | Zalipsky et al. |
| 5,399,346 A | 3/1995 | Anderson et al. |
| 5,723,118 A * | 3/1998 | Sebald ............... 424/85.2 |
| 5,882,679 A | 3/1999 | Needham |
| 6,130,318 A | 10/2000 | Wild et al. |
| 6,770,745 B2 * | 8/2004 | Burkly et al. ........ 530/388.22 |
| 2004/0259768 A1 * | 12/2004 | Lauermann ............ 514/2 |

FOREIGN PATENT DOCUMENTS

| WO | WO 2004/103295 | | 2/2004 |
| WO | WO 2004/021861 A2 | | 3/2004 |
| WO | WO 2004/021861 A3 | | 3/2004 |
| WO | WO 2004/103295 | * | 12/2004 |

OTHER PUBLICATIONS

LaPorte et al., PNAS, 2005, 102(6):1889-1894.*
Wang et al., Annu. Rev. Biophys. Biomol. Struct., 2006, 35:225-249 (abstract).*
Anderson, W. French, "Human Gene Therapy," *Nature*, vol. 392, Supplement, pp. 25-30, 1998.
Dong, Qu et al., "IL-9 Induces Chemokine Expression in Lung Epithelial Cells and Baseline Airway Eosinophilia in Transgenic Mice", *Eur. J. Immunol.* vol. 29, pp. 2130-2139, 1999.
Ecker and Crooke, "Combinatorial Drug Discovery: Which Methods Will Produce the Greatest Value?" *Biotechnology*, vol. 13, pp. 351-360, 1995.
Expert Panel on the Management of Asthma, "Definition and Diagnosis," *The Journal of Allergy and Clinical Immunology*, vol. 88, No. 3, Part 2, pp. 425-438, Sep. 1991.
Flotte, Terence R., "Prospects for Virus-Based Gene Therapy for Cystic Fibrosis," *Journal of Bioenergetics and Biomembranes*, vol. 25, No. 1, pp. 37-42, 1993.
Fraley and Papahadjopoulos, "New Generation Liposomes: The Engineering of an Efficient Vehicle for Intracellular Delivery of Nucleic Acids," *TIBS*, pp. 77-80, Mar. 1981.
Goeddel, David, V., "Systems for Heterologous Gene Expression," *Methods in Enzymology*, vol. 185, pp. 3-7, 1990.
Henderson, William R. Jr., Soluble IL-4 Receptor Inhibits Airway Inflammation Following Allergen Challenge in a Mouse Model of Asthma[1,] *J. Immunol.*, vol. 164, pp. 1086-1095, 2000.
Hopp, Thomas P. et al, "A Short Polypeptide Marker Sequence Useful for Recombinant Protein Identification and Purification", *BioTechnology*, vol. 6, pp. 1204-1210, 1988.
Huang, Shau-Ku et al., IL-13 Expression at the Sites of Allergen Challenge in Patients with Asthma, *J. Immunol.*, vol. 155, pp. 2688-2694, 1995.
Jellinek et al., "Potent 2'-Amino-2'-deoxypyrimidine RNA Inhibitors of Basic Fibroblast Growth Factor", *Biochemistry*, vol. 34, pp. 11363-11372, 1995.
Jolly, Douglas, "Viral Vector Systems for Gene Therapy," *Cancer Gene Therapy*, vol. 1, No. 1, pp. 51-64, 1994.
Krishenbaum et al., "Highly Efficient Gene Transfer into Adult Ventricular Myocytes by Recombinant Adenovirus," *Journal of Clinical Investigation*, vol. 92, pp. 381-387, 1993.
Lin et al., "Modified RNA Sequence Pools for in vitro Selection," *Nucleic Acids Research*, vol. 22, No. 24, pp. 5229-5234, 1994.
Longphre, M. et al., "Allergen-induced IL-9 directly stimulates mucin transcription in respiratory epithelial cells", *J. Clin. Invest*, vol. 104, pp. 1375-1382, 1999.
Michael et al., "Binding-incompetent Adenovirus Facilities Molecular Conjugate-Mediated Gene Transfer by the Receptor-Mediated Endocytosis Pathway," *The Journal of Biological Chemistry*, vol. 268, No. 10, pp. 6866-6869, 1993.
Miller and Rosman, "Improved Retroviral Vectors for Gene Transfer and Expression," *Biotechniques*, vol. 7, No. 9, pp. 980-990, 1989.
Morishita et al., "Novel and Effective Gene Transfer Technique for Study of Vascular Renin Angiotensin System," *Journal of Clinical Investigation*, vol. 91, pp. 2580-2585, 1993.
O'Byrne and Inman, "Airway Hyperresponsiveness," *Chest*, vol. 123, No. 3, pp. 411S-416S, Mar. 2003.
Pagratis et al., "Potent 2'-amino-, and 2'-Fluoro-2'-Deoxyribonucleotide RNA Inhibitors of Keratinocyte Growth Factor," *Nature Biotechnology*, vol. 15, pp. 68-73, Jan. 1997.

(Continued)

*Primary Examiner*—Gary B Nickol
*Assistant Examiner*—Xiaozhen Xie
(74) *Attorney, Agent, or Firm*—DLA Piper LLP (US)

(57) ABSTRACT

Chimeric polypeptide antagonists that include an interleukin-4 (IL-4) mutein linked to an interleukin-9 (IL-9) mutein are provided, as are polynucleotides encoding the IL-4 and IL-9 chimeric mutein antagonists. Also provided are methods of using the chimeric mutein antagonists and encoding polypeptides to reduce or inhibit the responsiveness of a cell to a cytokine such as IL-4, IL-9 and/or interleukin-13. Methods using the compositions to treat disorders such as pulmonary disorders (e.g., asthma) also are provided.

35 Claims, No Drawings

OTHER PUBLICATIONS

Postma et al., "Genetic Susceptibility to Asthma—Bronchial Hyperresponsiveness Coinherited with a Major Gene for Atopy," *The New England Journal of Medicine*, vol. 333, pp. 894-900, 1995.

Tam et al., "Biological Availability and Nuclease Resistance Extend the in vitro activity of a phosphorothioate-3'hydroxypropylamine Oligonucleotide," *Nucleic Acids Research*, vol. 22, No. 6, pp. 977-986, 1994.

Ulbrecht et al., "High Serum IgE Concentrations: Association with HLA-DR and Markers on Chromosome 5q31 and Chromosome 11q13," *Journal of Allergy and Clinical Immunology*, vol. 99, pp. 828-836, 1997.

Verma and Somia, "Gene Therapy-Promises, Problems and Prospects," *Nature*, vol. 389, pp. 239-242, Sep. 18, 1997.

Wilson, James M., "Adenoviruses as Gene-Delivery Vehicles," *Molecular Medicine*, vol. 334, No. 18, pp. 1185-1187, 1996.

Ying et al., "Expression of IL-4 and IL-5 mRNA and Protein Product by $CD4^+$ and $CD8^+$ T Cells, Eosinophils, and Mast Cells in Bronchial Biopsies Obtained from Atopic and Nonatopic (Intrinsic) Asthmatics," *The Journal of Immunology*, vol. 158, pp. 3539-3544, 1997.

Zhu et al., "Pulmonary Expression of Interleukin-13 Causes Inflammation, Mucus Hypersecretion, Subepithelial, Fibrosis, Pysiologic Abnormalities, and Eotaxin Production," *The Journal of Clinical Investigation*, vol. 103, No. 6, pp. 779-788, Mar. 1999.

\* cited by examiner

SEQUENCE LISTING

```
<160> NUMBER OF SEQ ID NOS: 7

<210> SEQ ID NO 1
<211> LENGTH: 885
<212> TYPE: DNA
<213> ORGANISM: Artificial sequence
<220> FEATURE:
<223> OTHER INFORMATION: Polynucleotide encoding His6TEV-IL4RA/IL9RA

<400> SEQUENCE: 1
atgcttctgg ccatggtcct tacctctgcc ctgctcctgt gctccgtggc aggccaaggc      60
catcatcacc atcaccatga ctacgacatc cccaccaccg aaaacctgta cttccagggg     120
cacaagtgcg atatcaacct tacaggagat catcaaaact tgaacagcct cacagagcag     180
aagactctgt gcaccgagtt gaccgtaaca gacatctttg ctgcctccaa gaacacaact     240
gagaaggaaa ccttctgcag ggctgcgact gtgctccggc agttctacag ccaccatgag     300
aaggacactc gctgcctggg tgcgactgca cagcagttcc acaggcacaa gcagctgatc     360
cgattcctga acggctcga caggaacctc tggggcctgg cgggcttgaa ttcctgtcct     420
```

```
gtgaaggaag ccaaccagag tacgttggaa aacttcttgg aaaggctaaa gacgatcatg    480
gacgagaaag actcaaagtg ttcgagccag ggctgtccaa ccttggcggg gatcctggac    540
atcaacttcc tcatcaacaa gatgcaggaa gatccagctt ccaagtgcca ctgcagtgct    600
aatgtgacca gttgtctctg tttgggcatt ccctctgaca actgcaccag accatgcttc    660
agtgagagac tgtctcagat gaccaatacc accatgcaaa caagataccc actgattttc    720
agtcgggtga aaaatcagt tgaagtacta agaacaaca agtgtccata ttttcctgt       780 gaacagccat gcaaccaaac cacggcaggc aacgcgctga catttctgga gagtcttctg    840
gaaattttca agaaagaaaa gatgagaggg atgagaggca agata                    885
```

<210> SEQ ID NO 2
<211> LENGTH: 295
<212> TYPE: PRT
<213> ORGANISM: Artificial sequence
<220> FEATURE:
<223> OTHER INFORMATION: His6TEV-IL4RA/IL9RA chimeric mutein

<400> SEQUENCE: 2

```
Met Leu Leu Ala Met Val Leu Thr Ser Ala Leu Leu Cys Ser Val
1               5                   10                  15

Ala Gly Gln Gly His His His His His His Asp Tyr Asp Ile Pro Thr
            20                  25                  30

Thr Glu Asn Leu Tyr Phe Gln Gly His Lys Cys Asp Ile Thr Leu Gln
        35                  40                  45

Glu Ile Ile Lys Thr Leu Asn Ser Leu Thr Glu Gln Lys Thr Leu Cys
    50                  55                  60

Thr Glu Leu Thr Val Thr Asp Ile Phe Ala Ala Ser Lys Asn Thr Thr
65                  70                  75                  80

Glu Lys Glu Thr Phe Cys Arg Ala Ala Thr Val Leu Arg Gln Phe Tyr
                85                  90                  95

Ser His His Glu Lys Asp Thr Arg Cys Leu Gly Ala Thr Ala Gln Gln
            100                 105                 110

Phe His Arg His Lys Gln Leu Ile Arg Phe Leu Lys Arg Leu Asp Arg
        115                 120                 125

Asn Leu Trp Gly Leu Ala Gly Leu Asn Ser Cys Pro Val Lys Glu Ala
    130                 135                 140

Asn Gln Ser Thr Leu Glu Asn Phe Leu Glu Arg Leu Lys Thr Ile Met
145                 150                 155                 160

Asp Glu Lys Asp Ser Lys Cys Ser Ser Gln Gly Cys Pro Thr Leu Ala
                165                 170                 175

Gly Ile Leu Asp Ile Asn Phe Leu Ile Asn Lys Met Gln Glu Asp Pro
            180                 185                 190

Ala Ser Lys Cys His Cys Ser Ala Asn Val Thr Ser Cys Leu Cys Leu
        195                 200                 205

Gly Ile Pro Ser Asp Asn Cys Thr Arg Pro Cys Phe Ser Glu Arg Leu
    210                 215                 220

Ser Gln Met Thr Asn Thr Thr Met Gln Thr Arg Tyr Pro Leu Ile Phe
225                 230                 235                 240

Ser Arg Val Lys Lys Ser Val Glu Val Leu Lys Asn Asn Lys Cys Pro
                245                 250                 255

Tyr Phe Ser Cys Glu Gln Pro Cys Asn Gln Thr Thr Ala Gly Asn Ala
            260                 265                 270

Leu Thr Phe Leu Glu Ser Leu Leu Glu Ile Phe Lys Lys Glu Lys Met
```

275                 280                 285
Arg Gly Met Arg Gly Lys Ile
        290                 295

<210> SEQ ID NO 3
<211> LENGTH: 882
<212> TYPE: DNA
<213> ORGANISM: Artificial sequence
<220> FEATURE:
<223> OTHER INFORMATION: Polynucleotide encoding His6TEV-IL9RA/IL4RA

<400> SEQUENCE: 3

| | | |
|---|---|---|
| atgcttctgg ccatggtcct tacctctgcc ctgctcctgt gctccgtggc aggccaaggc | 60 |
| catcatcacc atcaccatga ctacgacatc cccaccaccg aaaacctgta cttccagggg | 120 |
| tgtccaacct tggcggggat cctggacatc aacttcctca tcaacaagat gcaggaagat | 180 |
| ccagcttcca agtgccactg cagtgctaat gtgaccagtt gtctctgttt gggcattccc | 240 |
| tctgacaact gcaccagacc atgcttcagt gagagactgt ctcagatgac caataccacc | 300 |
| atgcaaacaa gatacccact gattttcagt cgggtgaaaa aatcagttga agtactaaag | 360 |
| aacaacaagt gtccatattt ttcctgtgaa cagccatgca accaaaccac ggcaggcaac | 420 |
| gcgctgacat ttctggagag tcttctggaa attttcaaga agaaaagat gagagggatg | 480 |
| agaggcaaga tacacaagtg cgatatcacc ttacaggaga tcatcaaaac tttgaacagc | 540 |
| ctcacagagc agaagactct gtgcaccgag ttgaccgtaa cagacatctt tgctgcctcc | 600 |
| aagaacacaa ctgagaagga aaccttctgc agggctgcga ctgtgctccg gcagttctac | 660 |
| agccaccatg agaaggacac tcgctgcctg ggtgcgactg cacagcagtt ccacaggcac | 720 |
| aagcagctga tccgattcct gaaacggctc acaggaacc tctggggcct ggcgggcttg | 780 |
| aattcctgtc ctgtgaagga agccaaccag agtacgttgg aaaacttctt ggaaaggcta | 840 |
| aagacgatca tggacgagaa agactcaaag tgttcgagct ga | 882 |

<210> SEQ ID NO 4
<211> LENGTH: 293
<212> TYPE: PRT
<213> ORGANISM: Artificial sequence
<220> FEATURE:
<223> OTHER INFORMATION: His6TEV-IL9RA/IL4RA chimeric mutein

<400> SEQUENCE: 4

Met Leu Leu Ala Met Val Leu Thr Ser Ala Leu Leu Cys Ser Val
1               5                   10                  15

Ala Gly Gln Gly His His His His His His Asp Tyr Asp Ile Pro Thr
            20                  25                  30

Thr Glu Asn Leu Tyr Phe Gln Gly Cys Pro Thr Leu Ala Gly Ile Leu
        35                  40                  45

Asp Ile Asn Phe Leu Ile Asn Lys Met Gln Glu Asp Pro Ala Ser Lys
    50                  55                  60

Cys His Cys Ser Ala Asn Val Thr Ser Cys Leu Cys Leu Gly Ile Pro
65                  70                  75                  80

Ser Asp Asn Cys Thr Arg Pro Cys Phe Ser Glu Arg Leu Ser Gln Met
                85                  90                  95

Thr Asn Thr Thr Met Gln Thr Arg Tyr Pro Leu Ile Phe Ser Arg Val
            100                 105                 110

Lys Lys Ser Val Glu Val Leu Lys Asn Asn Lys Cys Pro Tyr Phe Ser
        115                 120                 125

-continued

```
Cys Glu Gln Pro Cys Asn Gln Thr Thr Ala Gly Asn Ala Leu Thr Phe
    130                 135                 140

Leu Glu Ser Leu Leu Glu Ile Phe Lys Lys Glu Lys Met Arg Gly Met
145                 150                 155                 160
Arg Gly Lys Ile His Lys Cys Asp Ile Thr Leu Gln Glu Ile Ile Lys
                165                 170                 175
Thr Leu Asn Ser Leu Thr Glu Gln Lys Thr Leu Cys Thr Glu Leu Thr
            180                 185                 190
Val Thr Asp Ile Phe Ala Ala Ser Lys Asn Thr Thr Glu Lys Glu Thr
        195                 200                 205
Phe Cys Arg Ala Ala Thr Val Leu Arg Gln Phe Tyr Ser His His Glu
    210                 215                 220
Lys Asp Thr Arg Cys Leu Gly Ala Thr Ala Gln Gln Phe His Arg His
225                 230                 235                 240
Lys Gln Leu Ile Arg Phe Leu Lys Arg Leu Asp Arg Asn Leu Trp Gly
                245                 250                 255
Leu Ala Gly Leu Asn Ser Cys Pro Val Lys Glu Ala Asn Gln Ser Thr
            260                 265                 270
Leu Glu Asn Phe Leu Glu Arg Leu Lys Thr Ile Met Asp Glu Lys Asp
        275                 280                 285
Ser Lys Cys Ser Ser
    290

<210> SEQ ID NO 5
<211> LENGTH: 255
<212> TYPE: PRT
<213> ORGANISM: Artificial sequence
<220> FEATURE:
<223> OTHER INFORMATION: IL9RA/IL4RA chimeric mutein antagonist lacking
      a signal sequence

<400> SEQUENCE: 5

Gln Gly Cys Pro Thr Leu Ala Gly Ile Leu Asp Ile Asn Phe Leu Ile
1               5                   10                  15

Asn Lys Met Gln Glu Asp Pro Ala Ser Lys Cys His Cys Ser Ala Asn
            20                  25                  30

Val Thr Ser Cys Leu Cys Leu Gly Ile Pro Ser Asp Asn Cys Thr Arg
        35                  40                  45

Pro Cys Phe Ser Glu Arg Leu Ser Gln Met Thr Asn Thr Thr Met Gln
    50                  55                  60

Thr Arg Tyr Pro Leu Ile Phe Ser Arg Val Lys Lys Ser Val Glu Val
65                  70                  75                  80

Leu Lys Asn Asn Lys Cys Pro Tyr Phe Ser Cys Glu Gln Pro Cys Asn
                85                  90                  95

Gln Thr Thr Ala Gly Asn Ala Leu Thr Phe Leu Glu Ser Leu Leu Glu
            100                 105                 110

Ile Phe Lys Lys Glu Lys Met Arg Gly Met Arg Gly Lys Ile His Lys
        115                 120                 125

Cys Asp Ile Thr Leu Gln Glu Ile Ile Lys Thr Leu Asn Ser Leu Thr
    130                 135                 140

Glu Gln Lys Thr Leu Cys Thr Glu Leu Thr Val Thr Asp Ile Phe Ala
145                 150                 155                 160

Ala Ser Lys Asn Thr Thr Glu Lys Glu Thr Phe Cys Arg Ala Ala Thr
                165                 170                 175

Val Leu Arg Gln Phe Tyr Ser His His Glu Lys Asp Thr Arg Cys Leu
            180                 185                 190
```

```
Gly Ala Thr Ala Gln Gln Phe His Arg His Lys Gln Leu Ile Arg Phe
        195                 200                 205

Leu Lys Arg Leu Asp Arg Asn Leu Trp Gly Leu Ala Gly Leu Asn Ser
        210                 215                 220

Cys Pro Val Lys Glu Ala Asn Gln Ser Thr Leu Glu Asn Phe Leu Glu
225                 230                 235                 240

Arg Leu Lys Thr Ile Met Asp Glu Lys Asp Ser Lys Cys Ser Ser
                245                 250                 255

<210> SEQ ID NO 6
<211> LENGTH: 822
<212> TYPE: DNA
<213> ORGANISM: Artificial sequence
<220> FEATURE:
<223> OTHER INFORMATION: Polynucleotide encoding an IL9RA/IL4RA
      chimeric mutein antagonist, including signal sequence

<400> SEQUENCE: 6
atgcttctgg ccatggtcct tacctctgcc ctgctcctgt gctccgtggc aggccaaggg      60
tgtccaacct tggcggggat cctggacatc aacttcctca tcaacaagat gcaggaagat     120
ccagcttcca agtgccactg cagtgctaat gtgaccagtt gtctctgttt gggcattccc     180
tctgacaact gcaccagacc atgcttcagt gagagactgt ctcagatgac caataccacc     240
atgcaaacaa gataccccact gattttcagt cgggtgaaaa aatcagttga agtactaaag     300
aacaacaagt gtccatattt ttcctgtgaa cagccatgca accaaaccac ggcaggcaac     360
gcgctgacat ttctggagag tcttctggaa attttcaaga agaaaagat gagagggatg     420 agaggcaaga tacacaagtg cgatatcacc ttacaggaga tcatcaaaac tttgaacagc     480
ctcacagagc agaagactct gtgcaccgag ttgaccgtaa cagacatctt tgctgcctcc     540
aagaacacaa ctgagaagga aaccttctgc agggctgcga ctgtgctccg gcagttctac     600
agccaccatg agaaggacac tcgctgcctg ggtgcgactg cacagcagtt ccacaggcac     660
aagcagctga tccgattcct gaaacggctc gacaggaacc tctggggcct ggcgggcttg     720
aattcctgtc ctgtgaagga agccaaccag agtacgttgg aaaacttctt ggaaaggcta     780
aagacgatca tggacgagaa agactcaaag tgttcgagct ga                       822

<210> SEQ ID NO 7
<211> LENGTH: 273
<212> TYPE: PRT
<213> ORGANISM: Artificial sequence
<220> FEATURE:
<223> OTHER INFORMATION: IL9RA/IL4RA chimeric mutein antagonist,
      including signal sequence

<400> SEQUENCE: 7

Met Leu Leu Ala Met Val Leu Thr Ser Ala Leu Leu Leu Cys Ser Val
1               5                   10                  15

Ala Gly Gln Gly Cys Pro Thr Leu Ala Gly Ile Leu Asp Ile Asn Phe
            20                  25                  30

Leu Ile Asn Lys Met Gln Glu Asp Pro Ala Ser Lys Cys His Cys Ser
        35                  40                  45

Ala Asn Val Thr Ser Cys Leu Cys Leu Gly Ile Pro Ser Asp Asn Cys
    50                  55                  60

Thr Arg Pro Cys Phe Ser Glu Arg Leu Ser Gln Met Thr Asn Thr Thr
65                  70                  75                  80

Met Gln Thr Arg Tyr Pro Leu Ile Phe Ser Arg Val Lys Lys Ser Val
```

```
                        85                    90                    95
Glu Val Leu Lys Asn Asn Lys Cys Pro Tyr Phe Ser Cys Glu Gln Pro
                100                  105                110
Cys Asn Gln Thr Thr Ala Gly Asn Ala Leu Thr Phe Leu Glu Ser Leu
                115                  120                125
Leu Glu Ile Phe Lys Lys Glu Lys Met Arg Gly Met Arg Gly Lys Ile
                130                  135                140
His Lys Cys Asp Ile Thr Leu Gln Glu Ile Ile Lys Thr Leu Asn Ser
145                  150                  155                160
Leu Thr Glu Gln Lys Thr Leu Cys Thr Glu Leu Thr Val Thr Asp Ile
                165                  170                175
Phe Ala Ala Ser Lys Asn Thr Thr Glu Lys Glu Thr Phe Cys Arg Ala
                180                  185                190
Ala Thr Val Leu Arg Gln Phe Tyr Ser His His Glu Lys Asp Thr Arg
                195                  200                205
Cys Leu Gly Ala Thr Ala Gln Gln Phe His Arg His Lys Gln Leu Ile
                210                  215                220
Arg Phe Leu Lys Arg Leu Asp Arg Asn Leu Trp Gly Leu Ala Gly Leu
225                  230                  235                240
Asn Ser Cys Pro Val Lys Glu Ala Asn Gln Ser Thr Leu Glu Asn Phe
                245                  250                255
Leu Glu Arg Leu Lys Thr Ile Met Asp Glu Lys Asp Ser Lys Cys Ser
                260                  265                270
Ser
```

INTERLEUKIN-9 AND INTERLEUKIN-4 CHIMERIC ANTAGONIST MUTEINS AND METHODS OF USING SAME

CROSS REFERENCE TO RELATED APPLICATION(S)

This application claims the benefit of priority under 35 U.S.C. § 119(e) of U.S. Ser. No. 60/612,275 filed Sep. 22, 2004, the entire content of which is incorporated herein by reference.

BACKGROUND OF THE INVENTION

1. Field of the Invention

The invention relates generally to compositions useful for treating modulating an immune response, and more specifically to chimeric interleukin-4 (IL-4) and interleukin-9 (IL-9) muteins that act as antagonists of interleukin-4, interleukin-9, and interleukin-13 activity, and to methods of using such IL-4 and IL-9 chimeric antagonist muteins to modulate a cytokine-mediated response of a cell and to ameliorate a disorder associated with cytokine-mediated responsiveness.

2. Background Information

Interleukin-9 (IL-9), interleukin-4 (IL-4) and interleukin-13 (IL-13) are cytokines produced by activated T-cells upon antigen stimulation. Asthma is characterized by reversible airflow obstruction and airway hyper-responsiveness (AHR), associated with an infiltration of the bronchial mucosa with activated T-lymphocytes (T-cells), and eosinophils. These cells, along with resident airway mast cells, secrete a variety of cytokines and mediators that play a fundamental role in the pathogenesis of the disease (1,2).

A number of studies suggest that IL-9, as a mediator of Th2-dependent immune responses, has a role in asthma. Human linkage analysis showed an association between the IL-9 gene and elevated serum levels of IgE production and airway hyper-responsiveness (3,4). IL-9 transgenic mice exhibit many characteristics of human asthma, and have a strikingly robust peribronchial and perivascular eosinophilia after allergen challenge. The eosinophilia was coincident with the up-regulation in lung epithelial cells of eotaxin, MIP-1 and MCP-1, MCP-3, and MCP-5, which are chemotactic for eosinophils (5). Other evidence for the role of IL-9 in asthma includes studies of the ability of IL-9 to stimulate mucin secretion by airway epithelial cells (6). Taken together, these studies illustrate and support the role of IL-9 in regulating many clinical hallmarks of asthma and allergic inflammation.

IL-4 and IL-13 are considered pivotal to the development of allergic inflammation and asthma. Studies conducted with animals deficient in either cytokine, or employing reagents that neutralize either IL-4 or IL-13 function, have elucidated the important role these cytokines play in regulating the primary and secondary immune response leading to airway inflammation and airway hyper-responsiveness (7,8). Cumulatively, these data suggest that IL-4 and IL-13 have overlapping as well as independent roles in the allergic airways response.

Decreased IL-9, IL-4, and IL-13 activity can decrease Th2 polarization of the T-cell response, decrease eosinophil survival and neutrophil activity, and attenuate mucus production by airway epithelial cells. These effects, in turn, can reduce airway hyper-reactivity and remodeling, while increasing gas exchange and clearance, and, therefore, can provide an effective therapeutic modality for several lung diseases, including, for example, asthma, chronic obstructive pulmonary disease (emphysema and chronic bronchitis), and related pulmonary conditions. As such, targeting of IL-9, IL-4, and IL-13 can provide a significant therapeutic benefit as compared to the targeting any of these cytokine, alone. Thus, a need exists for compositions that can modulate the effect of IL-9, IL-4, and IL-13 on cells.

SUMMARY OF THE INVENTION

The present invention relates to a chimeric polypeptide that includes an interleukin-4 (IL-4) mutein receptor antagonist operatively linked to an interleukin-9 (IL-9) mutein receptor antagonist. The chimeric polypeptide is characterized, in part, in that it can specifically disrupt the formation of an IL-4 receptor, an IL-9 receptor, an interleukin-13 (IL-13) receptor, or a combination thereof, for example, by binding to an IL-4 or IL-9 α polypeptide and reducing or preventing association of the α polypeptide with an IL-2 receptor γ polypeptide to form a functional IL-4, IL-9 and/or IL-13 receptor. As such, a chimeric polypeptide of the invention, or a polynucleotide encoding the chimeric polypeptide, is useful, for example, for reducing or inhibiting the specific binding of IL-4, IL-9 and/or IL-13 to an IL-4, IL-9 and/or IL-13 receptor on a cell. Since the binding of such interleukins to their specific receptors can be associated with pathologic conditions such as asthma and other pulmonary disorders, and with particular cancers such as leukemias, the compositions of the invention can be useful for ameliorating such pathologic conditions.

A chimeric polypeptide of the invention can contain the IL-4 mutein receptor antagonist component positioned N-terminal to the IL-9 mutein receptor antagonist, or can contain the IL-9 mutein receptor antagonist component positioned N-terminal to the IL-4 mutein receptor antagonist. Such chimeric polypeptides are exemplified by the polypeptides shown in SEQ ID NO:2 and SEQ ID NO:4, respectively, which comprise the IL-4 mutein (IL-4RA) and IL-9 mutein (IL-9RA) components, and further include a signal peptide sequence, a polyhistidine tag, and a tobacco etch virus (TEV) protease recognition site positioned N-terminal to the IL-4 and IL-9 components. The IL-4 and IL-9 components of the chimeric polypeptide can be directly linked (i.e., the C-terminus of one component directly linked to the N-terminus of the second component), or can be linked via a spacer molecule that operatively links the two components such that each maintains its respective IL-4, IL-9 and/or IL-13 antagonist activity. In one embodiment, the spacer molecule is a peptide, wherein the chimeric polypeptide comprising the spacer peptide comprises a fusion protein encoded by a polynucleotide. In another embodiment, the spacer molecule allows operative linkage of the IL-4 and IL-9 components via a chemical reaction.

A chimeric polypeptide of the invention can include one or more additional operatively linked moieties, which can be positioned at the N-terminus and/or the C-terminus of the chimeric polypeptide, can be positioned between the IL-4 component and the IL-9 component, and/or can be bound to an amino acid side chain of one or both of the IL-4 and IL-9 components. The moiety can be any type of molecule that can be linked to a polypeptide, including, for example, a peptide, a polynucleotide, a small organic or inorganic molecule, a carbohydrate, a lipid, or a combination of such molecules. For example, the moiety can be peptide tag (e.g., a polyhistidine tag, a myc tag, a FLAG tag, or a V5 tag), or other tag such as biotin (or avidin or streptavidin). Such a tag can provide a means to detect the presence of the chimeric polypeptide and/or to purify the chimeric polypeptide from a composition containing the chimeric polypeptide. A peptide moiety also can be provide a recognition site for a protease (e.g., a TEV protease recognition site). The moiety also can be a detectable label, which can allow for convenient detection of the chimeric polypeptide, for example, in a sample, in which case it can further provide a means to determine the amount of the chimeric polypeptide in the sample; or in a cell, in which case it can provide a means to detect binding of the chimeric polypeptide to an IL-4, IL-9 and/or IL-13 receptor, or to an IL-4 and/or IL-9 receptor α polypeptide, expressed by the cell; or in vivo, in which case it can provide a means to monitor distribution and/or localization in a subject to which the chimeric polypeptide was administered. A detectable label can comprise a radionuclide, a fluorescent moiety, a luminescent moiety, a chemiluminescent moiety, a paramagnetic moiety, an enzyme (or cognate substrate), a receptor (or cognate ligand), or any other molecule that conveniently can be detected when bound to the chimeric polypeptide.

A chimeric polypeptide of the invention can be present in a substantially purified (isolated) form, or can be formulated as a composition that includes one or more carriers. A carrier can be any substance in which it is desired to combine the chimeric polypeptide, including, for example, an aqueous or non-aqueous carrier (e.g., a buffer, physiologic saline, or ethanol), or can be stabilizing material (e.g., a carbohydrate) with which the chimeric polypeptide can be maintained in a dry (e.g., lyophilized) state. In one embodiment, the composition includes a physiologically acceptable carrier, a pharmaceutically acceptable carrier, or a combination thereof, wherein the composition can be used when it is desired to contact the chimeric polypeptide with cells and/or to administer the chimeric polypeptide to a subject (e.g., a human subject).

The present invention also relates to a polynucleotide encoding a chimeric polypeptide comprising an IL-4 mutein operatively linked to an IL-9 mutein. The polynucleotide can be DNA, RNA or a DNA/RNA hybrid, and can be single stranded or double stranded. Also provided are oligonucleotides useful for identifying a polynucleotide encoding a chimeric polypeptide of the invention, such oligonucleotides being characterized, in part, in that they can hybridize to a region of the polynucleotide comprising IL-4 encoding sequences and IL-9 encoding sequences, or to a nucleotide sequence complementary thereto. Polynucleotides of the invention are exemplified by a polynucleotide that encodes a chimeric polypeptide having an amino acid sequence as set forth in SEQ ID NO:2, SEQ ID NO:4, SEQ ID NO:5, or SEQ ID NO:7, and by the polynucleotides having a nucleotide sequence as set forth in SEQ ID NO:1, SEQ ID NO:3, and SEQ ID NO:6.

In one embodiment, a polynucleotide encoding a chimeric polypeptide of the invention is operatively linked to a heterologous nucleic acid molecule, which can be a functional nucleic acid molecule or can act as a tag to identify the presence of the polynucleotide. As such, a heterologous nucleic acid molecule can comprise or encode a transcriptional regulatory element (e.g., a promoter, an enhancer, or a silencer), a translational regulatory element (e.g., a Kozak consensus sequence, a start codon, a ribosome binding sequence, a stop codon, or a poly-adenylation signal), or a combination of transcriptional and/or translational regulatory elements. A heterologous nucleic acid molecule also can encode a peptide, which can function as a tag and/or a detectable label, or can function as a cellular localization domain, which facilitates transport of the expressed chimeric polypeptide into or out of a particular cellular compartment.

As disclosed herein, a polynucleotide of the invention can be useful for a gene therapy type procedure, wherein the polynucleotide is contacted with a cell under conditions such that the chimeric polypeptide of the invention is expressed, wherein the chimeric polypeptide can effect its antagonist activity. Accordingly, the polynucleotide can be contained in a vector, which can be a cloning vector or an expression vector, and which can be a prokaryotic vector, a eukaryotic vector, or a shuttle vector (e.g., a vector that can be passaged in both prokaryotic and eukaryotic cells, or in different types of eukaryotic cells). In one embodiment, the vector is an expression vector, which contains one or more regulatory elements that facilitate expression of the polynucleotide in cells or cell types of interest. The expression vector can be a viral vector or a plasmid vector, or can contain components of both. Also provided are host cells, which contain a polynucleotide encoding a chimeric polypeptide of the invention, wherein the polynucleotide can, but need not, be contained in a vector (e.g., an expression vector). In one aspect, the polynucleotide encoding the chimeric polypeptide is stably integrated into the genome of the host cell.

The present invention also provides a method of reducing or inhibiting cytokine responsiveness of a cell. Such a method can be performed using cells in culture (e.g., cells of an established cell line or cell culture, or cells of a subject ex vivo), or the cells can be contacted in vivo (e.g., in an experimental animal system, or in a subject suffering from a disorder associated with cellular responsiveness to the cytokine). The method can be practiced, for example, by contacting the cell with a chimeric polypeptide encoding an IL-4 mutein operatively linked to an IL-9 mutein, or by contacting the cell with a polynucleotide encoding the chimeric polypeptide, under conditions suitable for expression of the encoded chimeric polypeptide. Cytokine (particularly IL-4, IL-9 and/or IL-13) responsiveness of cells includes, for example, the increase or decrease in cell proliferation mediated by a cytokine, the increase or decrease in protein expression by a cell exposed to the cytokine, including, for example, increased cytokine expression by cell due to contact with IL-4, IL-9 and/or IL-13.

In various aspects, the cytokine responsiveness of the cell can be IL-4 responsiveness, IL-9 responsiveness, or IL-13 responsiveness, or the cell can be a responsive to combination of cytokines (e.g., IL-4 and IL-9, IL-4 and IL-13, or IL-9 and a second or more cytokine(s)). The cell to be contacted can be any cell that exhibits a response to a cytokine, particularly a response mediated by binding of the cytokine to a receptor expressed by the cell. As such, the cell can be, for example, a lymphocyte (e.g., a T lymphocyte or a B lymphocyte), a polymorphonuclear leukocyte (e.g., an eosinophil), a monocyte (e.g., a histiocyte), or a mast cell. The cell can be a normal cell (e.g., a mast cell) that, due to its cytokine responsiveness, contributes to a disorder (e.g., a pulmonary disorder such as asthma), or can be a cancer cell (e.g., a leukemia cell such as an erythroleukemia cell or a megakaryoblastic leukemia cell), wherein the cytokine responsiveness is manifest by abnormal proliferation.

Accordingly, the present invention also relates to a method of ameliorating a pathologic condition associated with cells expressing at least one receptor selected from an IL-4 receptor, an IL-9 receptor, or an IL-13 receptor in a subject. The subject can be any subject having cells that express an IL-4, IL-9 and/or IL-13 receptor, wherein responsiveness of the cells to a cytokine is associated with a pathologic condition. As such, the subject can be a vertebrate subject, including, for example, a mammalian subject, particularly a human subject suffering from a pathologic condition (e.g., a pulmonary disorder such as asthma or a cancer such as a leukemia). The method of ameliorating a pathologic condition can be practiced, for example, by administering to the subject a chimeric polypeptide antagonist comprising an IL-4 mutein and an IL-9 mutein, or an expressible polynucleotide encoding the chimeric polypeptide, in an amount sufficient to reduce or inhibit specific binding of IL-4, IL-9, IL-13, or a combination thereof to the receptor, thereby ameliorating the pathologic condition in the subject. A pathologic condition amenable to amelioration according to the present methods include, for example, pulmonary disorders such as asthma and chronic obstructive pulmonary disease (e.g., emphysema and chronic bronchitis), and allergic inflammatory responses. Additional pathologic conditions amenable to treatment according to the present methods include cancers such as leukemias and lymphomas (e.g., non-Hodgkin's lymphoma).

The present invention also relates to a method of making a chimeric polypeptide, which comprises an IL-4 mutein receptor antagonist operatively linked to an IL-9 mutein receptor antagonist. Such a method conveniently can be performed by expressing a polynucleotide encoding the chimeric polypeptide. For example, the polynucleotide, which can, but need not, be contained in a vector, can be contained in a host cell, which can be cultured under conditions whereby the polynucleotide is expressed and the chimeric polypeptide is produced. Accordingly, the invention provides an IL-4 mutein receptor antagonist operatively linked to an IL-9 mutein receptor antagonist, produced by such a method. Further, the method can include a step of purifying the chimeric polypeptide. As such, the invention also provides a purified IL-4 mutein receptor antagonist operatively linked to an IL-9 mutein receptor antagonist produced by such a method.

DETAILED DESCRIPTION OF THE INVENTION

The present invention is based on the discovery that a chimeric polypeptide comprising an interleukin-4 (IL-4) mutein (IL-4RA) and an interleukin-9 (IL-9) mutein (IL-9RA) acts as an antagonist of IL-4, IL-9 and IL-13 mediated responsiveness of cells involved in immune and inflammatory responses. Accordingly, in one embodiment, the invention provides a chimeric polypeptide that includes an IL-4 mutein receptor antagonist operatively linked to an IL-9 mutein receptor antagonist, which can specifically disrupt the formation of an IL-4 receptor, an IL-9 receptor, an interleukin-13 (IL-13) receptor. In another embodiment, the chimeric polypeptide comprises an IL-4RA or an IL-9RA operatively linked to an IL-9 or an IL-4 component, respectively. Also provided are polynucleotides encoding such chimeric mutein antagonists, as well as methods of using the chimeric polypeptide, or encoding polynucleotide, to reduce or inhibit the specific binding of IL-4, IL-9 and/or IL-13 to an IL-4, IL-9 and/or IL-13 receptor on a cell.

Chimeric recombinant muteins have been developed from a human IL-9 mutein (IL-9RA), which inhibits IL-9-induced cell proliferation, and human IL-4 mutein, which is mutated in two positions of its amino acid sequence (IL-4RA). IL-9RA and IL-4RA were designed to bind to their respective IL-9 and IL-4 receptor alpha chains, thereby competitively inhibiting binding of the wild-type cytokines to the receptor and/or reducing or inhibiting the association of the IL-4 and/or IL-9 α polypeptide with an IL-2 receptor γ polypeptide (thus preventing assembly of a functional IL-4, IL-9, and/or IL-13 receptor). Wild-type IL-9 signals through a two subunit receptor that consists of IL-9Rα and the common γ chain, which is a shared component of the receptor complexes for IL-2, IL-4, IL-7, IL-13, IL-15, and possibly others. In comparison, IL-4 signals through the IL-4Rα and the common γ chains. The IL-4Rα chain also is a functional signaling component of the IL-13 receptor complex.

Various disorders, including, for example, pulmonary disorders such as asthma, are associated with cell responsiveness to cytokines. As disclosed herein, IL-9, IL-4, and IL-13-mediated cellular activity, including, for example, cytokine induced cell proliferation, can be attenuated by inhibiting cytokine signaling through their respective cognate cell-surface receptors using operatively linked forms of IL-9RA and IL-4RA chimeric polypeptide antagonists (see Example 1). The IL-9RA and IL-4RA chimeric mutein antagonists competitively inhibit the abilities of wild type IL-9, IL-4, and IL-13 to signal by blocking binding of the cytokines to their respective receptors. Accordingly, the present invention provides chimeric polypeptides, including, for example, fusion proteins, that comprise an IL-9 mutein and an IL-4 mutein, polynucleotides encoding such IL-9 and IL-4 chimeric antagonist muteins, compositions comprising the polypeptides and/or polynucleotides, and methods of using the compositions, for example, to modulate cytokine-mediated responsiveness of a cell, and to ameliorate a pathologic condition associated with cytokine-mediated responsiveness.

The present invention provides reagents and methods of inhibiting immune responses mediated by IL-4, IL-9 and IL-13. For example, a purified protein preparation comprising a chimeric (fusion) protein, which includes of a modified IL-4 mutein receptor antagonist operatively linked to an IL-9 mutein receptor antagonist, is provided. The IL-4RA component of the fusion protein can be located N-terminal to the IL-9RA component ("IL-4RA/IL-9RA"; see, e.g., SEQ ID NO:2), or the IL-9RA component of the fusion protein can be located N-terminal to the IL-4RA ("IL-9RA/IL-4RA"; see, e.g., SEQ ID NO:4; see, also, SEQ ID NOS:5 and 7). As used herein, the designation of a chimeric polypeptide indicates the N-terminal to C-terminal orientation of the IL-4 and IL-9 components (e.g., "IL-4RA/IL-9RA" indicates that the IL-4 mutein is N-terminal to the IL-9 mutein); the designation "RA" indicates that component (e.g., IL-4) is a mutein (i.e., IL-4RA) that can act as a cytokine receptor antagonist. As disclosed herein, one or, preferably, both of the IL-4 and IL-9 components of the receptor antagonist is a mutein. As used herein, reference to "an IL-4RA and IL-9RA chimeric polypeptide" or "an IL-9RA and IL-4RA chimeric antagonist" or "an IL-4 and IL-9 mutein fusion protein" or the like means that the IL-4 component can be N-terminal or C-terminal to the IL-9 component in the chimeric mutein antagonist.

The term "operatively linked" is used herein to refer to two or more molecules that share a covalent or non-covalent interaction, wherein each molecule maintains some or all of the function that the molecule exhibits alone. The two or more molecules, which can be peptides (polypeptides), polynucleotides, or other molecules, can be linked directly to each other, or can be operatively linked via a linker (spacer) molecule. For example, a polynucleotide encoding a first peptide, e.g., IL-4RA, can be operatively linked to a polynucleotide encoding a heterologous peptide, e.g., IL-9RA, such that the nucleotide sequences are in frame. Upon expression of such a recombinant polynucleotide, the peptides are expressed as a fusion protein, wherein the IL-4 and IL-9 components are operatively linked, and the IL-4RA component of the fusion protein can specifically bind at least to an IL-4 receptor, particularly to an IL-4 receptor α polypeptide, and the IL-9RA component can specifically bind at least to an IL-9 receptor, particularly to an IL-9 receptor α polypeptide.

The term "fusion protein" or "chimeric polypeptide" or the like is used herein to mean two more peptides that are operatively linked. A fusion protein can be obtained, for example, by expression a recombinant polynucleotide encoding the fusion protein, or a chimeric protein can be obtained by chemically linking a first peptide (e.g., IL-4 or an IL-4RA) to a second (or other) peptide (e.g., IL-9 or an IL-9 mutein), or by chemically synthesizing the entire protein comprising the peptide components. A chimeric protein of the invention also can be obtained using a combination of such methods, including, for example, by expressing a fusion polypeptide comprising IL-4RA operatively linked to IL-9RA, then further chemically linking a peptide tag (e.g., a polyhistidine tag) to the fusion protein.

The term "operatively linked" also is used to refer to a recombinant polynucleotide containing two or more linked polynucleotides, each of which maintains a function characteristic of the polynucleotide. For example, a recombinant polynucleotide can comprise an IL-4RA coding sequence operatively linked to an IL-9RA coding sequences, wherein the coding sequences are in-frame and can be expressed as a fusion protein having IL-4RA activity and IL-9RA activity. A recombinant polynucleotide also can include, for example, a transcriptional promoter (or other regulatory element) operatively linked to a coding sequence, wherein the transcriptional promoter can drive expression of the coding sequence under the appropriate conditions for expression of a polynucleotide from the promoter. As such, a first polynucleotide coding sequence can be operatively linked to a second (or more) coding sequence such that a chimeric polypeptide can be expressed from the operatively linked coding sequences.

The term "peptide" or "polypeptide" or "protein" is used broadly herein to mean two or more amino acids linked by a peptide bond. Generally, a peptide of the invention comprises a chimeric polypeptide, although peptide fragments comprising the linked regions of two peptides are contemplated. A peptide generally contains at least about six amino acids, usually contains about ten amino acids, and can contain fifteen or more amino acids, particularly twenty or more amino acids. It should be recognized that the term "peptide" is not used herein to suggest a particular size or number of amino acids comprising the molecule, and that a peptide of the invention can contain up to several amino acid residues or more. As used herein, the term "substantially purified" or "substantially pure" or "isolated" means that the molecule being referred to, for example, a peptide or a polynucleotide, is in a form that is relatively free of proteins, nucleic acids, lipids, carbohydrates or other materials with which it is naturally associated (i.e., in nature). Generally, a substantially pure peptide, polynucleotide, or other molecule constitutes at least twenty percent of a sample, generally constitutes at least about fifty percent of a sample, usually constitutes at least about eighty percent of a sample, and particularly constitutes about ninety percent or ninety-five percent or more of a sample.

As disclosed herein, the inclusion of a polyhistidine tag operatively linked to an IL-4RA and IL-9RA chimeric polypeptide provided a means to substantially purify the expressed chimeric polypeptide. Further, the inclusion of a TEV protease cleavage site between the tag and the IL-4RA and IL-9RA components provided a means to cleave the tag from the chimeric polypeptide antagonist (see, e.g., SEQ ID NOS:2 and 4). A determination that a peptide or a polynucleotide of the invention is substantially pure can be made using well known methods, for example, by performing electrophoresis and identifying the particular molecule as a relatively discrete band. A substantially pure polynucleotide, for example, can be obtained by cloning the polynucleotide, or by chemical or enzymatic synthesis. A substantially pure peptide can be obtained, for example, by a method of chemical synthesis, or using methods of protein purification, followed by proteolysis and, if desired, further purification by chromatographic or electrophoretic methods.

A chimeric polypeptide of the invention can correspond to an amino acid sequence of an IL-4 mutein and/or IL-9 mutein, or can vary from the mutein sequence, for example, by containing one or more D-amino acids in place of a corresponding L-amino acid; or by containing one or more amino acid analogs, for example, an amino acid that has been derivatized or otherwise modified at its reactive side chain. Similarly, one or more peptide bonds in the peptide can be modified. In addition, a reactive group at the amino terminus or the carboxy terminus or both can be modified. As such, the chimeric polypeptide antagonists can be modified, for example, to have improved stability to a protease, an oxidizing agent or other reactive material the peptide may encounter in a biological environment, and, therefore, can be particularly useful in performing a method of the invention. Of course, the peptides can be modified to have decreased stability in a biological environment such that the period of time the peptide is active in the environment is reduced.

The sequence of a chimeric polypeptide of the invention also can be modified in comparison to the corresponding sequence in an IL-4RA and/or IL-9RA component by incorporating a conservative amino acid substitution for one or a few amino acids in the peptide component. Conservative amino acid substitutions include the replacement of one amino acid residue with another amino acid residue having relatively the same chemical characteristics, for example, the substitution of one hydrophobic residue such as isoleucine, valine, leucine or methionine for another, or the substitution of one polar residue for another, for example, substitution of arginine for lysine; or of glutamic for aspartic acid; or of glutamine for asparagine; or the like, provided that the substitution does not result in a loss of IL-4, IL-9, and/or IL-13 antagonist activity of the chimeric polypeptide antagonist.

Modified IL-4 mutein receptor antagonists are described, for example, in U.S. Pat. Nos. 5,723,118 and 6,130,318, each of which is incorporated herein by reference). Modified IL-9 mutein receptor antagonists are described, for example, in International Application No. PCT/US2004/015168, which is incorporated herein by reference. As disclosed, mutations can be introduced into the D helix, including, for example, a substitution of lysine to glutamic acid at position 126 (K126E) and a substitution of glutamine for lysine at position 133 (Q133K) in IL-9 (or any other mutation(s) as disclosed in Int'l Appl. No. PCT/US2004/015168), to generate a double mutein IL9 and IL4 chimeric receptor antagonist. Methods for determining that a substitution at one or more positions of IL-4 and/or IL-9 results in a mutein antagonist useful for preparing a chimeric polypeptide antagonist of the invention are disclosed herein (see Example 1) and otherwise known in the art (see, e.g., U.S. Pat. Nos. 5,723,118 and 6,130,318, and Int'l. Appl. No. PCT/US2004/015168). For example, the capacity of the IL-4RA and IL-9RA mutein fusion proteins to reduce or inhibit the proliferative response of immune cells was assessed using proliferative assays as outlined in Example 1, and expressed as an "Inhibitory Concentration 50%" ($IC_{50}$). Generally, a chimeric polypeptide antagonist of the present invention can prevent the assembly of human IL-4 and IL-9 receptors and neutralize their capacity to prevent immune cell proliferation with a preferred $IC_{50}$ ranging from about 0.1 nM to 10 µM, including, for example, about 1.0 nM to 100 nM, or about 0.5 nM to 1 µM.

Also provided are polynucleotides encoding an IL-4RA and IL-9RA chimeric antagonist mutein, including, for example„a polynucleotide encoding an IL-4RA/IL-9RA fusion protein (see, e.g., SEQ ID NO:1) and a polynucleotide encoding an IL-9RA/IL-4RA fusion protein (see, e.g., SEQ ID NO:3 and SEQ ID NO:6). Accordingly, the invention further provides vectors (e.g., expression vectors) containing a polynucleotide encoding an IL-4 and IL-9 chimeric antagonist mutein, as well as host cells containing such polynucleotides and/or vectors. In addition, the invention provide methods of making an IL-4 and IL-9 mutein fusion protein by culturing such a host cell under conditions suitable for expression of the antagonist. Such a method can further include purifying the antagonist from the host cell culture, thus providing a means to obtain a substantially purified antagonist.

The term "polynucleotide" is used broadly herein to mean a sequence of two or more deoxyribonucleotides or ribonucleotides that are linked together by a phosphodiester bond. As such, the term "polynucleotide" includes RNA and DNA, which can be a gene or a portion thereof, a cDNA, a synthetic polydeoxyribonucleic acid sequence, or the like, and can be single stranded or double stranded, as well as a DNA/RNA hybrid. Furthermore, the term "polynucleotide" as used herein includes naturally occurring nucleic acid molecules, which can be isolated from a cell, as well as synthetic molecules, which can be prepared, for example, by methods of chemical synthesis or by enzymatic methods such as by the polymerase chain reaction (PCR). In various embodiments, a polynucleotide of the invention can contain nucleoside or nucleotide analogs, or a backbone bond other than a phosphodiester bond (see above).

In general, the nucleotides comprising a polynucleotide are naturally occurring deoxyribonucleotides, such as adenine, cytosine, guanine or thymine linked to 2'-deoxyribose, or ribonucleotides such as adenine, cytosine, guanine or uracil linked to ribose. However, a polynucleotide also can contain nucleotide analogs, including non-naturally occurring synthetic nucleotides or modified naturally occurring nucleotides. Such nucleotide analogs are well known in the art and commercially available, as are polynucleotides containing such nucleotide analogs (Lin et al., *Nucl. Acids Res.* 22:5220-5234 (1994); Jellinek et al., *Biochemistry* 34:11363-11372 (1995); Pagratis et al., *Nature Biotechnol.* 15:68-73 (1997), each of which is incorporated herein by reference).

The covalent bond linking the nucleotides of a polynucleotide generally is a phosphodiester bond. However, the covalent bond also can be any of numerous other bonds, including a thiodiester bond, a phosphorothioate bond, a peptide-like bond or any other bond known to those in the art as useful for linking nucleotides to produce synthetic polynucleotides (see, for example, Tam et al., *Nucl. Acids Res.* 22:977-986 (1994); Ecker and Crooke, *BioTechnology* 13:351360 (1995), each of which is incorporated herein by reference). The incorporation of non-naturally occurring nucleotide analogs or bonds linking the nucleotides or analogs can be particularly useful where the polynucleotide is to be exposed to an environment that can contain a nucleolytic activity, including, for example, a tissue culture medium or upon administration to a living subject, since the modified polynucleotides can be less susceptible to degradation.

A polynucleotide comprising naturally occurring nucleotides and phosphodiester bonds can be chemically synthesized or can be produced using recombinant DNA methods, using an appropriate polynucleotide as a template. In comparison, a polynucleotide comprising nucleotide analogs or covalent bonds other than phosphodiester bonds generally will be chemically synthesized, although an enzyme such as T7 polymerase can incorporate certain types of nucleotide analogs into a polynucleotide and, therefore, can be used to produce such a polynucleotide recombinantly from an appropriate template (Jellinek et al., supra, 1995).

Where a polynucleotide encodes a peptide, for example, a chimeric polypeptide comprising an IL-4 and/or IL-9 mutein, the coding sequence can be contained in a vector, wherein it can be operatively linked to appropriate regulatory elements, including, if desired, a tissue specific promoter or enhancer. The encoded peptide can be further operatively linked, for example, to peptide tag such as a polyhistidine (e.g., His6) tag or the like, which can facilitate identification of expression of the chimeric polypeptide in a sample (e.g., in a target cell). A polyhistidine tag peptide can be detected using a divalent cation such as nickel ion, cobalt ion, or the like. Additional peptide tags include, for example, a FLAG epitope, which can be detected using an anti-FLAG antibody (see, for example, Hopp et al., *BioTechnology* 6:1204, 1988; U.S. Pat. No. 5,011,912, each of which is incorporated herein by reference); a c-myc epitope, which can be detected using an antibody specific for the epitope; biotin, which can be detected using streptavidin or avidin; and glutathione S-transferase, which can be detected using glutathione. Such tags, which can be operatively linked to the N-terminus, C-terminus, or both of a chimeric IL4 and/or IL-9 mutein, can provide the additional advantage that they can facilitate isolation of the operatively linked chimeric polypeptide, for example, where it is desired to obtain the chimeric polypeptide in a substantially purified form. As such, the polynucleotides of the invention can provide a convenient means to obtain desired amounts of the chimeric polypeptides (e.g., sufficient quantities for therapeutic use).

The polynucleotides of the invention, which can be in a vector, can be contained in a host cell, or can be isolated free of other cellular components such as membrane components, proteins, and lipids. Isolated polynucleotides can be obtained, for example, from such host cells using standard nucleic acid purification techniques, or can be synthesized using an amplification technique (e.g., PCR) or using an automatic synthesizer. For example, restriction enzymes and probes can be used to identify and isolate a polynucleotide encoding an IL-4 and IL-9 chimeric mutein antagonist polypeptide.

A polynucleotide encoding an IL-4 and IL-9 chimeric mutein antagonist can be contained in a vector, which can facilitate manipulation of the polynucleotide, including introduction of the polynucleotide into a target cell. The vector can be a cloning vector, which is useful for maintaining the polynucleotide, or can be an expression vector, which contains, in addition to the polynucleotide, regulatory elements useful for expressing the encoded chimeric antagonist polypeptide. An expression vector can contain the expression elements necessary to achieve, for example, sustained transcription of the encoding polynucleotide, or the regulatory elements can be operatively linked to the polynucleotide prior to its being cloned into the vector.

An expression vector (or the polynucleotide) generally contains or encodes a promoter sequence, which can provide constitutive or, if desired, inducible or tissue specific or developmental stage specific expression of the encoding polynucleotide, a poly-A recognition sequence, and a ribosome recognition site or internal ribosome entry site, or other regulatory elements such as an enhancer, which can be tissue specific. The vector also can contain elements required for replication in a prokaryotic (e.g., bacterial) or eukaryotic (e.g., insect, yeast (e.g., *Pichia*) and/or mammalian) host system or both, as desired. Such vectors, which include plasmid vectors and viral vectors such as bacteriophage, baculovirus, retrovirus, lentivirus, adenovirus, vaccinia virus, semliki forest virus and adeno-associated virus vectors, are well known and can be purchased from a commercial source (Promega, Madison Wis.; Stratagene, La Jolla Calif.; GIBCO/BRL, Gaithersburg Md.; Invitrogen Corp., Carlsbad Calif.) or can be constructed by one skilled in the art (see, for example, *Meth. Enzymol.*, Vol. 185, Goeddel, ed. (Academic Press, Inc., 1990); Jolly, *Canc. Gene Ther.* 1:51-64, 1994; Flotte, *J. Bioenerg. Biomemb.* 25:37-42, 1993; Kirshenbaum et al., *J. Clin. Invest.* 92:381-387, 1993, each of which is incorporated herein by reference).

An inducible promoter such as the tetracycline (tet) promoter can be particularly useful for driving expression of a polynucleotide encoding an IL-4 and IL-9 mutein fusion protein. Upon administration of tetracycline, or a tetracycline analog, to a subject containing a polynucleotide operatively linked to a tet inducible promoter, expression of the encoded chimeric polypeptide is induced, whereby the chimeric polypeptide can effect its IL-4, IL-9 and/or IL-13 antagonist activity. Alternatively, or in addition, the polynucleotide can be operatively linked to tissue specific regulatory element, for example, a lung epithelial cell specific regulatory element, such that expression of an encoded peptide is restricted to the lung cells in an individual, or to lung cells in a mixed population of cells in culture, for example, an organ culture. In such a case, the encoded chimeric polypeptide can further contain a signal peptide, such that the chimeric polypeptide is exported extracellularly, where it can effect its antagonist activity on cytokine responsive cells.

Viral expression vectors can be particularly useful for introducing a polynucleotide into a cell, particularly a cell in a subject. Viral vectors provide the advantage that they can infect host cells with relatively high efficiency and can infect specific cell types. For example, a polynucleotide encoding a chimeric polypeptide antagonist of the invention can be cloned into a baculovirus vector, which then can be used to infect an insect host cell, thereby providing a means to produce large amounts of the encoded chimeric polypeptide. The viral vector also can be derived from a virus that infects cells of an organism of interest, for example, vertebrate host cells such as mammalian, avian or piscine host cells. Viral vectors can be particularly useful for introducing a polynucleotide useful in performing a method of the invention into a target cell. Viral vectors have been developed for use in particular host systems, particularly mammalian systems and include, for example, retroviral vectors, other lentivirus vectors such as those based on the human immunodeficiency virus (HIV), adenovirus vectors, adeno-associated virus vectors, herpesvirus vectors, vaccinia virus vectors, and the like (see Miller and Rosman, *BioTechniques* 7:980-990, 1992; Anderson et al., *Nature* 392:25-30 Suppl., 1998; Verma and Somia, *Nature* 389:239-242, 1997; Wilson, *New Engl. J. Med.* 334:1185-1187 (1996), each of which is incorporated herein by reference).

A polynucleotide, which can be contained in a vector, can be introduced into a cell by any of a variety of methods known in the art (Sambrook et al., "Molecular Cloning: A laboratory manual" (Cold Spring Harbor Laboratory Press 1989); Ausubel et al., "Current Protocols in Molecular Biology", John Wiley and Sons, Baltimore, Md. (1987, and supplements through 1995), each of which is incorporated herein by reference). Such methods include, for example, transfection, lipofection, microinjection, electroporation and, with viral vectors, infection; and can include the use of liposomes, microemulsions or the like, which can facilitate introduction of the polynucleotide into the cell and can protect the polynucleotide from degradation prior to its introduction into the cell. The selection of a particular method will depend, for example, on the cell into which the polynucleotide is to be introduced, as well as whether the cell is isolated in culture, or is in a tissue or organ in culture or in situ.

Introduction of a polynucleotide into a cell by infection with a viral vector is particularly advantageous in that it can efficiently introduce the nucleic acid molecule into a cell ex vivo or in vivo (see, for example, U.S. Pat. No. 5,399,346, which is incorporated herein by reference). Moreover, viruses are very specialized and can be selected as vectors based on an ability to infect and propagate in one or a few specific cell types. Thus, their natural specificity can be used to target the nucleic acid molecule contained in the vector to specific cell types. As such, a vector based on an HIV can be used to infect T cells, a vector based on an adenovirus can be used, for example, to infect respiratory epithelial cells, a vector based on a herpesvirus can be used to infect neuronal cells, and the like. Other vectors, such as adeno-associated viruses can have greater host cell range and, therefore, can be used to infect various cell types, although viral or non-viral vectors also can be modified with specific receptors or ligands to alter target specificity through receptor mediated events.

A chimeric protein of the invention can be used to modulate the responsiveness of a cell to a cytokine, particularly to IL-4, IL-9, and/or IL-13, depending on the responsiveness of the cell. In one embodiment, the chimeric protein can inhibit the proliferative response of erythroleukemia cells (e.g., TF-1 cells) to IL-4, or to IL-13, or to both IL-4 and IL-13, with an $IC_{50}$ (concentration that inhibits proliferation of 50% of the cells) at a concentration of about 0.1 nM to about 10 FM (e.g., about 0.5 nM to about 1 µM, or about 1.0 nM to about 100 nM). In another embodiment, the chimeric protein can inhibit the proliferative response of megakaryoblastic leukemia cells (e.g., Mo7e cells) to IL-4, or to IL-9, or to both IL-4 and IL-9, with an $IC_{50}$ of about 0.1 nM to about 10 µM (e.g., about 0.5 nM to about 1 µM, or about 1.0 nM to about 100 nM). In still another embodiment, the chimeric protein can inhibit the proliferative response of B cells, or of T cells, or of both B cells and T cells (e.g., human B cells and/or T cells) to IL-4 with an $IC_{50}$ of about 0.1 nM to about 10 µM (e.g., about 0.5 nM to about 1 µM, or about 1.0 nM to about 100 nM).

In various aspects, the method of modulating the responsiveness of cells to a cytokine provides methods of preventing a pathologic condition and therapeutic methods for ameliorating a pathologic condition associated with such cellular responsiveness. The pathologic conditions can be manifest as an aberrant immune response and/or an aberrant inflammatory response, including, for example, an allergic inflammatory reaction, asthma, and chronic obstructive pulmonary disorders (e.g., emphysema and bronchitis). Accordingly, the invention provides a method of treating a disorder in which IL-4 and/or IL-9 receptors are expressed in cells associated with the disorder, particularly disorders of vertebrates, including mammals (e.g., humans). In one embodiment, the method is performed by administering a chimeric protein that antagonizes IL-4, IL-9 and/or IL-13 mediated activity to a subject to be treated (e.g., a human), wherein the chimeric protein is administered in an amount sufficient to antagonize IL-4, IL-9 and/or IL-13-mediated activity, thereby ameliorating the pathologic condition. In another embodiment, the method is performed by administering an expressible polynucleotide encoding a chimeric protein that antagonizes IL-4, IL-9 and/or IL-13 mediated activity to a subject to be treated (e.g., a human), wherein the polynucleotide, which can be contained in a vector, is administered such that it can enter cells in which the chimeric polypeptide can be expressed and released from the cells in an amount sufficient to antagonize IL-4, IL-9 and/or IL-13-mediated activity, thereby ameliorating the pathologic condition The present invention also provides compositions, including pharmaceutical compositions, which can be administered to a subject suffering from such a pathologic condition (e.g., a pulmonary disorder) associated with cytokine expression and/or cellular responsiveness to cytokines, particularly IL-4, IL-9, and/or IL-13. Such a composition of the invention includes a chimeric protein comprising, for example, an IL-4RA operatively linked to an IL-9RA, wherein the chimeric protein can specifically bind to an IL-4 receptor α polypeptide and/or an IL-9 receptor α polypeptide (thereby disrupting the assembly of a human IL-4, IL-9, and/or IL-13 receptor), or a polynucleotide encoding the chimeric protein, and a pharmaceutically acceptable carrier suitable for administration to the intended subject. As used herein, the term "specifically binds" means that two molecules form a complex that is relatively stable under physiologic conditions. The term is used herein in reference to an interleukin and its receptor (e.g., IL-4 and an IL-4 receptor), including to an interleukin mutein (e.g., IL-4RA) and a cognate interleukin receptor or component thereof (e.g., an IL-4 receptor α polypeptide). Specific binding can be characterized by a dissociation constant of at least about $1 \times 10^{-6}$ M, generally at least about $1 \times 10^{-7}$ M, usually at least about $1 \times 10^{-8}$ M, and particularly at least about $1 \times 10^{-9}$ M or $1'10^{-10}$ M or Specific binding generally is stable under physiological conditions, including, for example, conditions that occur in a living individual such as a human or other vertebrate or invertebrate, as well as conditions that occur in a cell culture such as used for maintaining mammalian cells or cells from another vertebrate organism or an invertebrate organism. Methods for determining whether two molecules specifically bind are well known and include, for example, equilibrium dialysis, surface plasmon resonance, two hybrid assays, and the like. Specific binding of a chimeric protein comprising, for example, an IL-4RA operatively linked to an IL-9RA chimeric polypeptide can be identified by detecting disruption of binding of an interleukin (e.g., IL-4) with its receptor, by detecting a reduction or inhibition of binding of an interleukin with a cognate receptor, and/or by detecting a reduction or inhibition of assembly of IL-4 and/or IL-9 α polypeptide with an IL-2 γ polypeptide to form a functional interleukin receptor.

As disclosed herein, composition of the invention can have use in treating a disorder associated with cytokine responsiveness of cells, including, for example, ameliorating pulmonary disorders such as asthma and bronchitis, as well as cancers such as leukemias and lymphomas. As such, the chimeric polypeptides and encoding polynucleotides are useful as medicaments for use in treating a subject suffering from a pathological condition associated with cytokine (e.g., IL-4, IL-9, and/or IL-13) induced cell responsiveness.

Pharmaceutically acceptable carriers are well known in the art and include, for example, aqueous solutions such as water or physiologically buffered saline or other solvents or vehicles such as glycols, glycerol, oils such as olive oil or injectable organic esters. A pharmaceutically acceptable carrier can contain physiologically acceptable compounds that act, for example, to stabilize or to increase the absorption of the conjugate. Such physiologically acceptable compounds include, for example, carbohydrates, such as glucose, sucrose or dextrans, antioxidants, such as ascorbic acid or glutathione, chelating agents, low molecular weight proteins or other stabilizers or excipients. One skilled in the art would know that the choice of a pharmaceutically acceptable carrier, including a physiologically acceptable compound, depends, for example, on the physico-chemical characteristics of the therapeutic agent and on the route of administration of the composition, which can be, for example, orally, via inhalation, or parenterally such as intravenously, and by injection, intubation, or other such method known in the art. In addition to an IL-4 and IL-9 chimeric mutein polypeptide, the pharmaceutical composition also can contain a second reagent such as a diagnostic reagent, nutritional substance, toxin, or therapeutic agent, for example, a cancer chemotherapeutic agent.

The chimeric polypeptide can be incorporated within an encapsulating material such as into an oil-in-water emulsion, a microemulsion, micelle, mixed micelle, liposome, microsphere or other polymer matrix (see, for example, Gregoriadis, "Liposome Technology", Vol. 1 (CRC Press, Boca Raton, Fla. 1984); Fraley, et al., *Trends Biochem. Sci.*, 6:77 (1981), each of which is incorporated herein by reference). Liposomes, for example, which consist of phospholipids or other lipids, are nontoxic, physiologically acceptable and metabolizable carriers that are relatively simple to make and administer. "Stealth" liposomes (see, for example, U.S. Pat. Nos. 5,882,679; 5,395,619; and 5,225,212, each of which is incorporated herein by reference) are an example of such encapsulating materials particularly useful for preparing a pharmaceutical composition useful for practicing a method of the invention, and other "masked" liposomes similarly can be used, such liposomes extending the time that the therapeutic agent remain in the circulation. Cationic liposomes, for example, also can be modified with specific receptors or ligands (Morishita et al., *J. Clin. Invest.*, 91:2580-2585 (1993), which is incorporated herein by reference). In addition, a polynucleotide agent can be introduced into a cell using, for example, adenovirus-polylysine DNA complexes (see, for example, Michael et al., *J. Biol. Chem.* 268:6866-6869 (1993), which is incorporated herein by reference).

The route of administration of a pharmaceutical composition containing a chimeric polypeptide (or encoding polynucleotide) of the invention will depend, in part, on the chemical structure of the molecule. Polypeptides and polynucleotides, for example, are not particularly useful when administered orally because they can be degraded in the digestive tract. However, methods for chemically modifying polypeptides, for example, to render them less susceptible to degradation by endogenous proteases or more absorbable through the alimentary tract are well known (see, for example, Blondelle et al., supra, 1995; Ecker and Crook, supra, 1995). In addition, a chimeric polypeptide can be prepared using D-amino acids, or can contain one or more domains based on peptidomimetics, which are organic molecules that mimic the structure of peptide domain; or based on a peptoid such as a vinylogous peptoid.

A pharmaceutical composition as disclosed herein can be administered to an individual by various routes including, for example, via inhalation, orally or parenterally, such as intravenously, intramuscularly, subcutaneously, intraorbitally, intracapsularly, intraperitoneally, intratracheally, intrarectally, intracistemally or by passive or facilitated absorption through the skin using, for example, a skin patch or transdermal iontophoresis, respectively. Furthermore, the pharmaceutical composition can be administered by injection, intubation, orally or topically, the latter of which can be passive, for example, by direct application of an ointment, or active, for example, using a nasal spray or inhalant, in which case one component of the composition is an appropriate propellant. A pharmaceutical composition also can be administered to the site of a pathologic condition, for example, intravenously or intra-arterially into a blood vessel supplying a tumor, or via inhalation for treatment of a pulmonary disorder.

The total amount of an agent to be administered in practicing a method of the invention can be administered to a subject as a single dose, either as a bolus or by infusion over a relatively short period of time, or can be administered using a fractionated treatment protocol, in which multiple doses are administered over a prolonged period of time. One skilled in the art would know that the amount of the pharmaceutical composition to treat a pathologic condition in a subject depends on many factors including the age and general health of the subject as well as the route of administration and the number of treatments to be administered. In view of these factors, the skilled artisan would adjust the particular dose as necessary. In general, the formulation of the pharmaceutical composition and the routes and frequency of administration are determined, initially, using Phase I and Phase II clinical trials.

The pharmaceutical composition can be formulated for oral formulation, such as a tablet, or a solution or suspension form; or can comprise an admixture with an organic or inorganic carrier or excipient suitable for enteral or parenteral applications, and can be compounded, for example, with the usual non-toxic, pharmaceutically acceptable carriers for tablets, pellets, capsules, suppositories, solutions, emulsions, suspensions, or other form suitable for use. The carriers, in addition to those disclosed above, can include glucose, lactose, mannose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition auxiliary, stabilizing, thickening or coloring agents and perfumes can be used, for example a stabilizing dry agent such as triulose (see, for example, U.S. Pat. No. 5,314,695).

As disclosed herein, the fusion protein antagonists of the invention can be provided in a pharmaceutical composition comprising a pharmaceutically acceptable carrier. The pharmaceutically acceptable carrier preferably is non-pyrogenic. The compositions can be administered alone or in combination with at least one other agent (e.g., a stabilizing compound), and can be administered in any sterile, biocompatible pharmaceutical carrier, including, for example, saline, buffered saline, dextrose, and water. A variety of aqueous carriers may be employed, e.g., 0.4% saline, 0.3% glycine, and the like. These solutions are sterile and generally free of particulate matter. These solutions can be sterilized by conventional, well known sterilization techniques (e.g., filtration). The compositions also can contain pharmaceutically acceptable auxiliary substances to approximate physiological conditions such as pH and buffering capacity. The concentration of the chimeric polypeptide antagonist in the pharmaceutical formulation can vary as desired, including, for example, from less than about 0.5% (e.g., 0.05%, 0.1%, or 0.25%) to about 20% (e.g., 1%, 2%, 3%, 4%, 5%, 10%, or 15%) by weight, and can be selected based, for example, on fluid volume, viscosities, or other parameter as is known in the art for a particular mode of administration selected. If desired, two or more different cytokine antagonists can be included in a formulation, including, for example, chimeric polypeptide antagonists having different dissociation constants ($K_d$) for IL-4 and/or IL-9 receptor binding.

The compositions can be administered to a patient alone, or in combination with other agents, drugs or hormones. In addition to the active ingredients, the pharmaceutical compositions can contain suitable pharmaceutically acceptable carriers comprising excipients and auxiliaries that facilitate processing of the active compounds into preparations which can be used pharmaceutically. Pharmaceutical compositions of the invention can be administered by any number of routes including, for example, oral, intravenous, intramuscular, intra-arterial, intramedullary, intrathecal, intraventricular, transdermal, subcutaneous, intraperitoneal, intratracheal, intranasal, parenteral, topical, sublingual, or rectally. Upon preparation, a pharmaceutical composition can be placed in an appropriate container and labeled for treatment of an indicated condition. Such labeling can include, for example, information-relevant to the amount, frequency, and/or method of administration.

The present invention also provides methods of ameliorating a pathologic condition associated with cells expressing at least one receptor selected from an IL-4 receptor, an IL-9 receptor, or an IL-13 receptor in a subject, by administering to the subject an IL-4 and IL-9 chimeric mutein polypeptide antagonist, or an expressible polynucleotide encoding the chimeric polypeptide, in an amount sufficient to reduce or inhibit specific binding of IL-4, IL-9 IL-13, or a combination thereof to the receptor, thereby ameliorating the pathologic condition in the subject. As used herein, the term "ameliorate," when used in reference to a pathologic condition, means that signs or symptoms associated with the condition are lessened. The signs or symptoms to be monitored will be characteristic of a particular pathologic condition and will be well known to skilled clinician, as will the methods for monitoring the signs and conditions. For example, where the pathologic condition is asthma, the skilled clinician will known that amelioration can be identified by detecting improvements in parameters such as airway hyper-responsiveness, and/or in airway inflammation including, for example, by detecting mast cell, eosinophil and/or lymphocyte recruitment. Amelioration of a pulmonary disorder such as asthma, bronchitis, and the like can be determined, for example, by the subject indicating that breathing is easier following administration of the chimeric polypeptide or encoding polynucleotide.

As disclosed herein, the methods of the invention provide a means to reduce or inhibit the responsiveness of cells to cytokines, particularly IL-4, IL-9 and/or IL-13. As used herein, the term "responsiveness of cells to a cytokine" means that the cells referred to express IL-4, IL-9 and/or IL-13 receptors, which specifically bind IL-4, IL-9 and/or IL-13 and mediate an effect on or by the cell. The effect can be any cellular effect associated with cytokine binding including, for example, cell proliferation and protein expression. The terms "reduce or inhibit" are used together herein because it is recognized that, in some cases, the level of cell responsiveness, upon contact with a chimeric polypeptide antagonist of the invention, can be reduced below a level that can be detected by a particular assay. As such, it may not be determinable using such an assay as to whether expression of a protein by the cell is reduced below the level of detection of the assay, or is completely inhibited. Regardless, however, a change will be measurable as compared to the level of the responsiveness of the cell in the absence of the chimeric polypeptide antagonist.

A pathologic condition amenable to amelioration according to the present methods include, for example, pulmonary disorders such as asthma and chronic obstructive pulmonary disease (e.g., emphysema and chronic bronchitis), allergic inflammatory responses, and cancers (e.g., leukemias and lymphomas). Features of asthma, for example, include recurrent episodes of respiratory symptoms; variable airflow obstruction that is often reversible, either spontaneously or with treatment; presence of airway hyper-reactivity; and chronic airway inflammation in which many cells and cellular elements, including, for example, mast cells, eosinophils, T lymphocytes, macrophages, neutrophils, and epithelial cells, are involved (see National Heart, Lung, and Blood Institute:

National Asthma Education and Prevention Program. Expert Panel Report Guidelines for the diagnosis and management of asthma. *J. Allergy Clin. Immunol.* 88:425-534, 1991; National Heart, Lung, and Blood Institute National Asthma Education Program Expert Panel Report II: Guidelines for the diagnosis and management of asthma; 1997. NIH Publication No. 97-4051A) While all of these features need not be present in any given asthmatic patient, and an absolute "minimum criteria" to establish a diagnosis of asthma has not been or widely agreed upon, the presence of airway hyper-reactivity is a common finding in patients with current symptoms and active asthma.

Asthma severity is graded into four categories based on the frequency of symptoms, peak flows, and the need for inhaled beta agonists: mild intermittent, mild persistent, moderate persistent, and severe persistent (Kavuru et al., "Asthma" (The Cleveland Clinic, January 2003), available on the world wide web (www) at "clevelandclinicmeded.com/diseasemanagement/pulmonary/asthma.asthma.htm"). Hyperinflation, the most common finding on a chest radiograph, has no diagnostic or therapeutic value. A chest radiograph should not be obtained unless complications of pneumonia, pneumothorax, or an endobronchial lesion are suspected. The correlation of severity between acute asthma and arterial blood gases is poor. Mild-to-moderate asthma is typically associated with respiratory alkalosis and mild hypoxemia on the basis of ventilation-perfusion mismatching. Severe hypoxemia is quite uncommon in asthma. Normocapnia and hypercapnia do imply severe airflow obstruction, with $FEV_1$ usually less than 25% of the predicted value.

Airway hyperresponsiveness is a characteristic feature of asthma and consists of an increased sensitivity of the airways to an inhaled constrictor agonist, a steeper slope of the dose-response curve, and a greater maximal response to the agonist (Byrne and Inman, *Chest*, 2003). Measurements of airway responsiveness are useful in making a diagnosis of asthma, particularly in patients who have symptoms that are consistent with asthma and who have no evidence of airflow obstruction. Certain inhaled stimuli, including, for example, environmental allergens, increase airway inflammation and enhance airway hyperresponsiveness. The changes in airway hyperresponsiveness in healthy subjects are of much smaller magnitude than those seen when asthmatic patients with persistent airway hyperresponsiveness. The pathogenesis of asthma, and amelioration due to treatment according to the present methods, can be followed by bronchoscopy, bronchoalveolar lavage, airway biopsy, measurement of airway gases, and other such methods known to the skilled clinician.

An amount of a chimeric polypeptide required to achieve a therapeutic benefit can be determined using methods as disclosed herein or otherwise known in the art. A therapeutically effective dose refers to the amount of antagonist that is used to effectively treat a disorder as compared with the efficacy that is evident in the absence of the therapeutically effective dose. A therapeutically effective dose can be estimated initially using an animal model (e.g., a rat, mouse, rabbit, dog, pig, or non-human primate model). An animal model also can be useful for determining an appropriate concentration range and route of administration, such that useful doses and routes for administration then can be identified for humans, for example, in clinical trials.

Therapeutic efficacy and toxicity, including, for example, an $ED_{50}$ (i.e., a dose that is therapeutically effective in 50% of a specified population) and $LD_{50}$ (the dose lethal to 50% of a population), of an IL-4 and IL-9 chimeric mutein antagonist can be determined using standard pharmaceutical procedures in cell cultures or experimental animals. The dose ratio of toxic to therapeutic effects (i.e., the therapeutic index) it can be expressed as the ratio, $LD_{50}/ED_{50}$. Generally, pharmaceutical compositions that exhibit large therapeutic indices are preferred. The data obtained from animal studies is used in formulating a range of dosages for human use. The dosage contained in such compositions is preferably within a range of circulating concentrations that include the $ED_{50}$ with little or no toxicity. The dosage varies within this range depending upon the dosage form employed, sensitivity of the patient, and the route of administration.

An exact dosage for treating a human subject, for example, will be determined by the practitioner, in light of factors related to the patient who requires treatment. Dosage and administration are adjusted to provide sufficient levels of the antagonist or to maintain the desired effect. Factors that can be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions can be administered every 3 to 4 days, every week, or once every two weeks depending on the half-life and clearance rate of the particular formulation. Effective in vivo dosages of an antagonist of the invention can be in the range of about 0.1 to 50 mg/kg, including, for example, about 1 μg/kg to about 5 mg/kg, or about 10 μg/kg to about 1 mg/kg, or about 100 to 250 μg/kg of patient body weight.

The following examples are intended to illustrate but not limit the invention.

EXAMPLE 1

IL-4 and IL-9 Chimeric Mutein Antagonists Inhibit Cytokine Induced Cell Proliferation This example demonstrates that an IL-4 and IL-9 chimeric mutein antagonists can inhibit cell proliferation due to IL-4 and/or IL-9.

Sequences

Exemplary polynucleotides encoding polyhistidine tagged IL-4RA/IL-9RA (SEQ ID NO:1) and IL-9RA/IL-4RA (SEQ ID NO:3) chimeric mutein antagonists, containing a TEV protease cleavage site between the tag and the IL-4 and IL-9 components, are provided, as are the encoded polypeptides (SEQ ID NOS:2 and 4, respectively). Also provided are an IL-9RA/IL-4RA chimeric polypeptide lacking a signal sequence (SEQ ID NO:5); and a polynucleotide sequence encoding an IL-9RA/IL-4RA chimeric mutein antagonist, including a signal sequence (SEQ ID NO:6), and the encoded polypeptide, including the signal sequence (SEQ ID NO:7).

Protein Purification

Purification of the polypeptides is exemplified by IL-4RA purification. Anti-IL4 antibody column was stored in 20% ethanol at 4° C. The anti-IL4 antibody column was used, and was equilibrated in running buffer at room temperature. A flow rate of about 2 ml per minute for a 1.5 cm diameter column was used. Buffers were as follows: "Running buffer" was phosphate buffered saline (PBS); "Elution buffer" was 200 mM Glycine, pH2.8; "Neutralization buffer" was a saturated solution of Tris base; "Cleaning solution: was 24% ethanol, 2% acetic acid.

Purification of the IL-4RA polypeptide was performed by running 3 column volumes of cleaning solution through the column, followed by 10 column volumes of PBS. The filtered sample was loaded, then 10 column volumes of PBS were passed over the column. IL-4RA was eluted using the elution buffer; the solution was neutralized immediately after collection with a few drops of Tris base. These steps were repeated for each purification run.

Purification of a HisTev tagged IL-9RA and IL-4RA chimeric receptor antagonist was performed using a chelating resin (e.g., Pharmacia Chelating SEPHAROSE resin) charged with a metal ion (e.g., nickel). The chelating resin was equilibrated in PBS (pH 7.0) supplemented to 500 mM NaCl to prevent non-specific binding of the tagged protein. Supernatant of cell cultures expressing the chimeric receptor antagonist were concentrated using a spin column with a molecular weight cut-off of ≧30,000 Daltons, then diluted 20-fold into PBS (pH 7.2) and concentrated a second time. A second dilution was performed and the supernatant was concentrated a third time to achieve about a 400-fold buffer exchange. The concentrated and exchanged supernatant was applied to an immobilized metal ion chromatography (IMAC) column, and washed with several column volumes of equilibration buffer. Non-tagged protein impurities that bound to the column were washed with equilibration buffer adjusted to 10-20 mM imidazole (pH 7.5) HisTev tagged IL-9RA and IL-4RA chimeric receptor antagonist then was eluted from the column suing PBS adjusted to 250 mM imidazole (pH 7.5).

TF-1 Cell Proliferation Assay for IL-4 and IL-13 Antagonism

TF-1 cells are a erythroleukemia cell line that respond to several pro-inflammatory cytokines by proliferation and, therefore, can be used to assess cytokine bioactivity. The proliferative response of TF-1 cells to IL-4 (0.5 ng/ml, 0.033 nM) or IL-13 (5 ng/ml, 0.416 nM) was used to assess the functional antagonistic activity of His6TEV-IL-4RA/IL-9RA (SEQ ID NO:2) and His6TEV-IL-9RA/IL-4RA (SEQ ID NO:4) chimeric polypeptides. It should be noted that the chimeric antagonist polypeptides were expressed in cells, which post-translationally remove the signal peptide. As such, while reference is made in this Example to His6TEV-IL-4RA/IL-9RA (SEQ ID NO:2) and His6TEV-IL-9RA/IL-4RA (SEQ ID NO:4), the chimeric polypeptides used in the experiments lack the signal peptide, which is shown as amino acid residues 1 to 18 in each of SEQ ID NOS:2 and 4.

TF-1 cells were cultured for 3 days in 96 well plates (10× 10⁴/well, 100 μl volume) in RPMI+10% serum with or without IL-4 or IL-13 and His6TEV-IL-4RA/IL-9RA (SEQ ID NO:2) or His6TEV-IL-9RA/IL-4RA (SEQ ID NO:4). GM-CSF treatment was used as a positive control. Twenty-four hours before the final reading, 10 μl AlamarBlue™ dye (10% volume) was added to each well. Fluorescence was determined at 530/590 nm using a WALLAC Victor 2 spectrofluorimeter. The "Inhibitory Concentration 50%" ($IC_{50}$) was calculated based on dose titration of the candidate antagonistic molecules. $IC_{50}$ values obtained using His6TEV-IL-4RA/IL-9RA (SEQ ID NO:2) and His6TEV-IL-9RA/IL-4RA (SEQ ID NO:4) in the presence of IL-4 or IL-13 are shown in Table 1 (below).

In further experiments, the ability of an untagged IL-9RA/IL-4RA (see, e.g., SEQ ID NOS:5 and 7; mutein antagonists lacking and containing the signal peptide, respectively) to inhibit IL-4 induced proliferation of TF-1 cells. As shown in Table 1, the untagged IL-9RA/IL-4RA chimeric polypeptide had an $IC_{50}$ of 0.6237 nM (n=3).

These results demonstrate that IL-4RA and IL-9RA chimeric mutein polypeptides act as antagonists of IL-4 and/or IL-13 induced cell proliferation of erythroleukemia cells.

Mo7e Cell Proliferation Assay for IL-4 and IL-9 Antagonism

Mo7e cells are a megakaryoblastic leukemia cell line, which, like the TF-1 cells, respond to a number of pro-inflammatory cytokines via proliferation. Mo7e cells also exhibit a proliferative response to IL-9 in addition to IL-4. The proliferative response of Mo7e cells to IL-9 (0.25 ng/ml, 17.8 pM) and IL-4 (0.5 ng/ml, 0.033 nM) was also examined to assess the functional antagonistic activity of His6TEV-IL-4RA/IL-9RA (SEQ ID NO:2) and His6TEV-IL-9RA/IL-4RA (SEQ ID NO:4) chimeric polypeptides. The Mo7e cell line was obtained from the Deutsche Sammlung von Mikroorganismen und Zellkulturen GmbH (Braunschweig, Germany) and maintained in RPMI-1640 with 10% fetal calf serum (RPMI-10), 10 ng/ml GM-CSF and penicillin.

Prior to experiments, Mo7e cells were starved of GM-CSF overnight and plated at $10^4$ cells/well in RPMI-10 cell culture media at a total volume of 100 ul/well. Cells were treated with His6TEV-IL-4RA/IL-9RA (SEQ ID NO:2) or His6TEV-IL-9RA/IL-4RA (SEQ ID NO:4) plus wild-type human IL-9 or IL-4 for 3 days. GM-CSF treatment was used as a positive control. Twenty-four hours before the final reading, 10 μl AlamarBlue™ dye (10% vol) was added to each well. Fluorescence was determined at 530/590 nm using a WALLAC Victor 2 spectrofluorimeter. The $IC_{50}$ was calculated based on dose titration of the candidate antagonistic molecules. The $IC_{50}$ values obtained using His6TEV-IL-4RA/IL-9RA (SEQ ID NO:2) and His6TEV-IL-9RA/IL-4RA (SEQ ID NO:4) chimeric polypeptides in the presence of wild-type IL-9 or wild-type IL4 are shown in Table 2 (below).

The ability of untagged IL-9RA/IL-4RA (see, e.g., SEQ ID NOS:5 and 7) to inhibit IL-9 induced proliferation of Mo7e cells also was examined. As shown in Table 2, the untagged IL-9RA/IL-4RA chimeric polypeptide had an $IC_{50}$ of 29.625 nM (n=2).

These results demonstrate that IL-4RA and IL-9RA chimeric mutein polypeptides act as antagonist of IL-4 and/or IL-9 induced cell proliferation of megakaryoblastic leukemia cells.

Primary T-Cell Proliferation Assay

T-cells are a key component of an allergic immune response, orchestrating the response of several inflammatory cell pathways, and are involved in the pathogenesis of asthma in humans. The proliferative response of primary T-cells to IL-4 was evaluated following pretreatment of the cells with His6TEV-IL-4RA/IL-9RA (SEQ ID NO:2) or His6TEV-IL-9RA/IL-4RA (SEQ ID NO:4) chimeric polypeptide. T-cells were isolated from peripheral blood and treated with PHA-P for 4 days to induce blast formation. The cells were washed and seeded in 96-well plates ($10^5$ cells per well). Phytohemmagluttinin (PHA) T-cell blasts were stimulated for 3 days with IL-4 (10 ng/ml, 0.667 nM) in the presence of varying concentrations of the chimeric mutein antagonist polypeptides. The incorporation of tritiated thymidine in the last 20 hours of incubation was used as an indicator of proliferation.

The $IC_{50}$ values obtained using His6TEV-IL-4RA/IL-9RA (SEQ ID NO:2) and His6TEV-IL-9RA/IL-4RA (SEQ ID NO:4) in the presence of wild-type IL-4 are shown in Table 3 (below). These results demonstrate that IL-4RA and IL-9RA chimeric mutein polypeptides acts as antagonist of IL-4 induced T-cell proliferation.

Primary B-Cell Proliferation Assay

T-cells affect B-cell proliferation and differentiation. B-cells are responsible for the production of antibody (as differentiated plasma cells) and are inextricably linked to T-cell activity in the asthmatic patient. The proliferative response of primary B-cells to IL-4 was examined following His6TEV-IL-4RA/IL-9RA (SEQ ID NO:2) and His6TEV-IL-9RA/IL-4RA (SEQ ID NO:4). B-cells were isolated from peripheral blood and treated with anti-CD40 MAb. The cells were seeded in 96-well plates ($10^5$ cells per well) and stimulated for 3 days with IL-4 (10 ng/ml, 0.667 nM) in the presence of varying concentrations of mutein antagonist molecules. The incorporation of tritiated thymidine in the last 20 hours of incubation was used as an indicator of proliferation.

The $IC_{50}$ values obtained using His6TEV-IL-4RA/IL-9RA (SEQ ID NO:2) and His6TEV-IL-9RA/IL-4RA (SEQ ID NO:4) in the presence of wild-type IL-4 are shown in Table 3 (below). These results demonstrate that IL-4RA and IL-9RA chimeric mutein polypeptides acts as antagonist of IL-4 induced B-cell proliferation.

TABLE 1

IL-9 and IL-4 Chimeric Antagonist Mutein Bioactivity Evaluation in TF-1 Cell Proliferation Assay

|  | TF-1/IL4 $IC_{50}$, nM | TF-1/IL13 $IC_{50}$, nM |
|---|---|---|
| His6TEV-IL-9RA/IL-4RA (4*) | 8.01 ± 1.73 (n = 3) | 20.14 ± 0 (n = 1) |
| His6TEV-IL-4RA/IL-9RA (3) | 20.66 ± 1.89 (n = 3) | 56.2 ± 0 (n = 1) |
| IL-9RA/IL-4RA (5) | 0.6237 nM (n = 3) |  |

*number in parentheses is SEQ ID NO:

TABLE 2

IL-9 and IL-4 Chimeric Antagonist Mutein Bioactivity Evaluation in Mo7e Cell Proliferation Assay

|  | Mo7e/IL9 $IC_{50}$, nM | Mo7e/IL4 $IC_{50}$, nM |
|---|---|---|
| His6TEV-IL-9RA/IL-4RA (4*) | 83.62 ± 24.73 (n = 2) | 10.13 ± 0.18 (n = 2) |
| His6TEV-IL-4RA/IL-9RA (3) | 570.75 ± 163.7 (n = 2) | 15.24 ± 1.36 (n = 2) |
| IL-9RA/IL-4RA (5) | 11.49 nM (n = 1) |  |

*number in parentheses is SEQ ID NO:

TABLE 3

IL-9 and IL-4 Chimeric Antagonist Mutein Bioactivity Evaluation Primary T-Cell and B-Cell Proliferation Assay

|  | B-cell $IC_{50}$, nM | T-cell blast $IC_{50}$, nM |
|---|---|---|
| His6TEV-IL-9RA/IL-4RA (4*) | 10.62 ± 5.71 (n = 3) | 33.98 ± 7.02 (n = 4) |
| His6TEV-IL-4RA/IL-9RA (3) | 16.34 ± 10.55 (n = 3) | 103.89 ± 46.99 (n = 4) |

*number in parentheses is SEQ ID NO:

REFERENCES CITED

Each of the following articles is incorporated herein by reference.

1. Ying et al., *J. Immunol.* 158: 3539-3544, 1997.
2. Huang et al., *J. Immunol.* 155: 2688-2694, 1995.
3. Ulbrecht et al., *J Allergy Clin Immunol* 199:828-836, 1997.
4. Postma et al., *New Engl. J. Med.* 333:894-900, 1995.
5. Dong et al., *Eur J Immunol* 29:2130-2139, 1999.
6. Longphre et al., *J Clin Invest* 104: 1375-1382, 1999.
7. Zhu et al., *J. Clin. Invest.* 103: 779-788, 1999.
8. Henderson et al., *J. Immunol.* 164: 1086-1095, 2000.

Although the invention has been described with reference to the above example, e understood that modifications and variations are encompassed within the spirit and the invention. Accordingly, the invention is limited only by the following claims.

What is claimed is:

1. A chimeric polypeptide, comprising an interleukin-4 (IL-4) mutein receptor antagonist operatively linked to an interleukin-9 (IL-9) mutein receptor antagonist, wherein the IL-4 mutein receptor antagonist comprises the amino acid sequence of wild-type human IL-4 with one or more of the amino acids at positions 121, 124 or 125 substituted with another natural amino acid, and the IL-9 mutein receptor antagonist comprises the amino acid sequence of wild-type human IL-9 with one or more of the amino acids at positions 126 or 133 substituted with another natural amino acid, wherein the IL-9 mutein receptor antagonist is positioned N-terminal to the IL-4 mutein receptor antagonist, and wherein the chimeric polypeptide reduces or inhibits the association of an interleukin with an IL-4 receptor, an IL-9 receptor, an interleukin-13 (IL-13) receptor, or a combination thereof.

2. The chimeric polypeptide of claim 1, wherein the IL-4 mutein receptor antagonist comprises a R121D substitution.

3. The chimeric polypeptide of claim 1, wherein the IL-4 mutein receptor antagonist comprises a Y124D substitution.

4. The chimeric polypeptide of claim 1, wherein the IL-4 mutein receptor antagonist comprises a R121D substitution and a Y124D substitution.

5. The chimeric polypeptide of claim 1, wherein the IL-9 mutein receptor antagonist comprises a K126E substitution.

6. The chimeric polypeptide of claim 1, wherein the IL-9 mutein receptor antagonist comprises a Q133K substitution.

7. The chimeric polypeptide of claim 1, wherein the IL-9 mutein receptor antagonist comprises a K126E and a Q133K substitution.

8. The chimeric polypeptide of claim 1, which has the amino acid sequence as set forth in SEQ ID NO: 4, SEQ ID NO: 5, or SEQ ID NO: 7.

9. The chimeric polypeptide of claim 1, further comprising a peptide tag selected from the group consisting of a polyhistidine tag, a myc tag, a FLAG epitope, a V5 tag, and a combination thereof.

10. The chimeric polypeptide of claim 1, further comprising a detectable label.

11. The chimeric polypeptide of claim 10, wherein the detectable label comprises a radionuclide, a fluorescent moiety, a luminescent moiety, a chemiluminescent moiety, a paramagnetic moiety, an enzyme, or a substrate.

12. The chimeric polypeptide of claim 1, which specifically binds an IL-4 receptor α polypeptide, an IL-9 receptor α polypeptide, or a combination thereof, thereby reducing or inhibiting assembly of a functional interleukin receptor.

13. The chimeric polypeptide of claim 1, which specifically binds an IL-4 receptor, an JL-9 receptor, or a combination thereof, thereby reducing or inhibiting specific binding of an interleukin to the IL-4 receptor, the IL-9 receptor, or the combination thereof.

14. A composition, comprising the chimeric polypeptide of claim 1 and a carrier.

15. The composition of claim 14, wherein the carrier comprises a physiologically acceptable carrier, a pharmaceutically acceptable carrier, or a combination thereof.

16. A polynucleotide encoding the chimeric polypeptide of claim 1.

17. The polynucleotide of claim 16, which encodes the chimeric polypeptide as set forth in SEQ ID NO: 4, SEQ ID NO: 5, or SEQ ID NO: 7.

18. The polynucleotide of claim 16, which comprises the nucleotide sequence as set forth in SEQ ID NO: 3 or SEQ ID NO: 6.

19. The polynucleotide of claim 16, which is operatively linked to a heterologous nucleic acid molecule.

20. The polynucleotide of claim 19, wherein the heterologous nucleic acid molecule comprises a transcriptional regulatory element, a translational regulatory element, or a combination thereof.

21. The polynucleotide of claim 19, wherein the heterologous nucleic acid molecule encodes a peptide.

22. The polynucleotide of claim 21, wherein the peptide comprises a tag, a cellular localization domain, or a combination thereof.

23. A vector, which comprises the polynucleotide of claim 16.

24. The vector of claim 23, which is an expression vector.

25. The vector of claim 24, wherein the expression vector is a prokaryotic expression vector, a eukaryotic expression vector, or a shuttle vector.

26. The vector of claim 23, which comprises a viral vector.

27. An isolated host cell, which comprises the polynucleotide of claim 16.

28. The host cell of claim 27, which comprises the vector of claim 23.

29. The host cell of claim 28, wherein the vector is an expression vector.

30. A method of making a chimeric polypeptide, which comprises an IL-4 mutein receptor antagonist operatively linked to an IL-9 mutein receptor antagonist, comprising expressing the polynucleotide of claim 16, thereby making the chimeric polypeptide.

31. The method of claim 30, which comprises culturing the host cell of claim 27 under conditions whereby the polynucleotide is expressed.

32. The method of claim 30, which comprises culturing the host cell of claim 29, under conditions suitable for expression of the polynucleotide.

33. A chimeric polypeptide, which comprises an IL-4 mutein receptor antagonist operatively linked to an IL-9 mutein receptor antagonist, wherein the IL-9 mutein receptor antagonist is positioned N-terminal to the IL-4 mutein receptor antagonist, produced by the method of claim 30.

34. The method of claim 30, further comprising purifying the chimeric polypeptide.

35. A purified chimeric polypeptide, which comprises an IL-4 mutein receptor antagonist operatively linked to an IL-9 mutein receptor antagonist, wherein the IL-9 mutein receptor antagonist is positioned N-terminal to the IL-4 mutein receptor antagonist, produced by the method of claim 34.

* * * * *

UNITED STATES PATENT AND TRADEMARK OFFICE
CERTIFICATE OF CORRECTION

| | | |
|---|---|---|
| PATENT NO. | : 7,635,754 B2 | Page 1 of 1 |
| APPLICATION NO. | : 11/026396 | |
| DATED | : December 22, 2009 | |
| INVENTOR(S) | : Boisvert et al. | |

It is certified that error appears in the above-identified patent and that said Letters Patent is hereby corrected as shown below:

Title Page, Item [*]

Delete the phrase "by 135 days" and insert -- by 286 days --.

In the claims, please amend claim 13 as follows:

13. The chimeric polypeptide of claim 1, which specifically binds an IL-4 receptor, an [JL-9] IL-9 receptor, or a combination thereof, thereby reducing or inhibiting specific binding of an interleukin to the IL-4 receptor, the IL-9 receptor, or the combination thereof.

Signed and Sealed this

Thirty-first Day of August, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,635,754 B2 | Page 1 of 1 |
| APPLICATION NO. | : 11/026396 | |
| DATED | : December 22, 2009 | |
| INVENTOR(S) | : Boisvert et al. | |

It is certified that error appears in the above-identified patent and that said Letters Patent is hereby corrected as shown below:

On the Title Page:

The first and sole Notice should read --

Subject to any disclaimer, the term of this patent is extended or adjusted under 35 U.S.C. 154(b) by 286 days.

Column 32, lines 53-57, In the claims, please amend claim 13 as follows:

13. The chimeric polypeptide of claim 1, which specifically binds an IL-4 receptor, an [JL-9] IL-9 receptor, or a combination thereof, thereby reducing or inhibiting specific binding of an interleukin to the IL-4 receptor, the IL-9 receptor, or the combination thereof.

This certificate supersedes the Certificate of Correction issued August 31, 2010.

Signed and Sealed this

Twenty-eighth Day of September, 2010

David J. Kappos
*Director of the United States Patent and Trademark Office*